(12) United States Patent
Izraeli et al.

(10) Patent No.: US 8,841,266 B2
(45) Date of Patent: Sep. 23, 2014

(54) PHARMACEUTICAL COMPOSITION AND METHOD FOR REGULATING ABNORMAL CELLULAR PROLIFERATION

(75) Inventors: Shai Izraeli, ModiIn (IL); Ilan R. Kirsch, Seattle, WA (US); Ayelet Erez, Moshav Bnei Tzion (IL); Stefano Campaner, Milan (IT)

(73) Assignees: Tel Hashomer Medical Research Infrastructure and Services Ltd., Ramat-Gan (IL); The United States of America as represented by the Secretary of the Department of Health and Human Services National Institutes of Health Office of Technology Transfer, Washington, DC (US)

( * ) Notice: Subject to any disclaimer, the term of this patent is extended or adjusted under 35 U.S.C. 154(b) by 1892 days.

(21) Appl. No.: 12/085,023

(22) PCT Filed: Nov. 16, 2006

(86) PCT No.: PCT/IL2006/001324
§ 371 (c)(1),
(2), (4) Date: Jul. 19, 2010

(87) PCT Pub. No.: WO2007/057897
PCT Pub. Date: May 24, 2007

(65) Prior Publication Data
US 2010/0278797 A1  Nov. 4, 2010

Related U.S. Application Data

(60) Provisional application No. 60/737,384, filed on Nov. 17, 2005.

(51) Int. Cl.
*A01N 43/04* (2006.01)
*C12P 19/34* (2006.01)
*C12N 15/63* (2006.01)
*C07H 21/02* (2006.01)
*C07H 21/04* (2006.01)

(52) U.S. Cl.
USPC ............. 514/44; 435/6; 435/91.1; 435/91.31; 435/455; 514/1; 514/2; 536/23.1; 536/24.5

(58) Field of Classification Search
USPC ............ 435/6, 91.1, 91.31, 455; 514/1, 2, 44; 536/23.1, 24.5
See application file for complete search history.

(56) References Cited

U.S. PATENT DOCUMENTS

2002/0168638 A1  11/2002  Schlegel et al.
2003/0143732 A1   7/2003  Fosnaugh et al.
2006/0088532 A1*  4/2006  Alitalo et al. .............. 424/145.1
2007/0048301 A1*  3/2007  Bodary-Winter et al. . 424/143.1
2007/0105114 A1*  5/2007  Li et al. ............................. 435/6

OTHER PUBLICATIONS

Opalinska et al., Nature Rev., vol. 1, pp. 503-514 (2002).*
Office Action Dated Jul. 12, 2010 From the Israel Patent Office Re. Application No. 191416 and Its Translation Into English.
International Preliminary Report on Patentability Dated Jan. 22, 2009 From the International Bureau of WIPO Re.: Application No. PCT/IL2006/001324.
Aplan et al. "Structural Characterization of SIL, A Gene Frequently Disrupted in T-Cell Acute Lymphoblastic Leukemia", Molecular and Cellular Biology, 11(11): 5462-5469, Nov. 1991.
Erez et al. "The SIL Gene Is Essential for Survival of Cancer Cells Probably Through Its Function in Mitosis", Presented in the Ilanit (FISEB 2005) Meeting, Feb. 7-10, 2005. Abstract.
Izraeli et al. "Expression of the SIL Gene Is Correlated With Growth Induction and Cellular Proliferation", Cell Growth & Differentiation, 8: 1171-1179, Nov. 1997.
Tuschl "The siRNA User Guide: Selection of siRNA Duplexes From the Target mRNA Sequence", Max Planck Institute for Biophysical, Retrieved From the Internet: <www.mpibpc.gwdg.de/abteilungen/100/105/sRNAuserguide.pdf>.
Campaner et al. "SIL Phosphorylation in A Pin1 Binding Domain Affects the Duration of the Spindle Checkpoint", Molecular and Cellular Biology, XP002597453, 25(15): 6660-6672, Aug. 2005. Fig.11.
Izraeli et al. "Expression of the Sil Gene Is Correlated With Growth Induction and Cellular Proliferation", Cell Growth & Differentiation,XP002597455, 8: 1171-1179, Nov. 1997.
Communication Pursuant to Rules 70(2) and 70a(2) EPC Dated Sep. 21, 2010 From the European Patent Office Re. Application No. 06809878.9.
Colaizzo-Anas et al. "Cloning and Characterization of the SIL Promoter", Biochimica et Biophysica Acta, XP002597456, 1625(2): 207-213, Jan. 27, 2003.
Erez et al. "Sil Overexpression in Lung Cancer Characterizes Tumors With Increased Mitotic Activity", Oncogene, XP002597454, 23(31): 5371-5377, Jul. 8, 2004. Abstract.
Campaner et al. "Sil Phosphorylation in A Pin1 Binding Domain Affects the Duration of the Spindle Checkpoint", Molecular and Cellular Biology, 25(15): 6660-6672, 2005.

* cited by examiner

*Primary Examiner* — Jane Zara
(74) *Attorney, Agent, or Firm* — Browdy and Neimark, PLLC

(57) ABSTRACT

A method of treating a disease associated with a cell population which proliferates abnormally in a subject is disclosed. The method comprises administering to the subject a therapeutically effective amount of at least one modulator capable of modulating in the cell population a level and/or activity of a polypeptide having an amino acid sequence at least 60 percent similar to SEQ ID NO: 5, as determined using the Standard protein-protein BLAST [blastp] software of the NCBI.

10 Claims, 17 Drawing Sheets
(15 of 17 Drawing Sheet(s) Filed in Color)

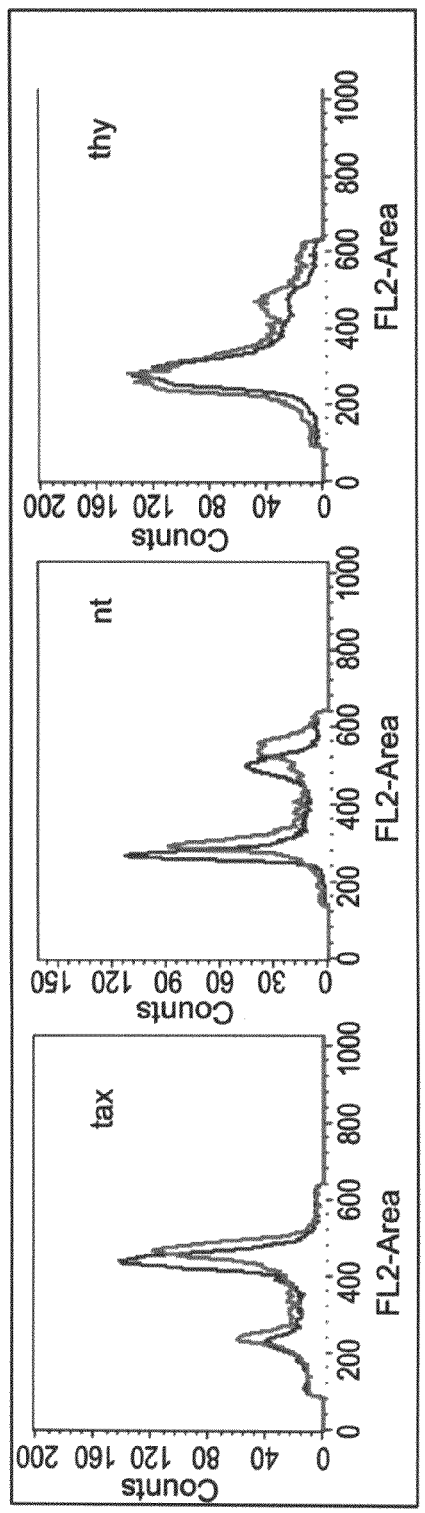
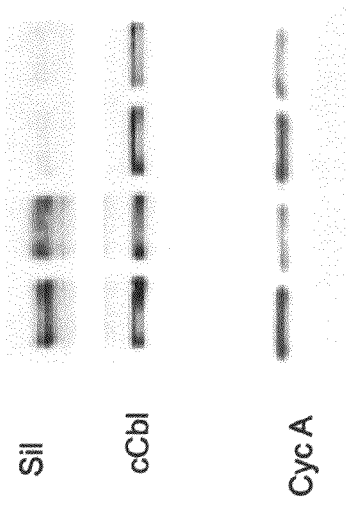
Fig. 4a
Fig. 4b

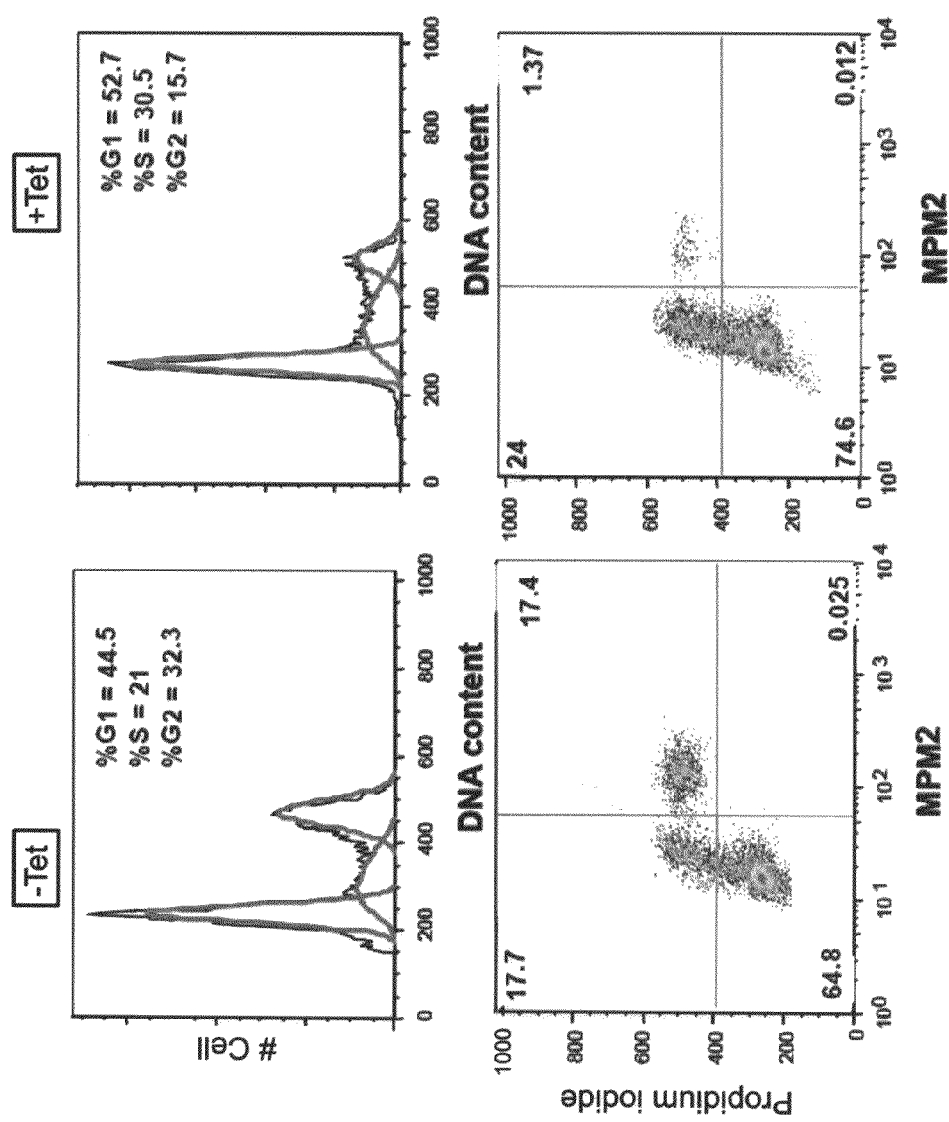

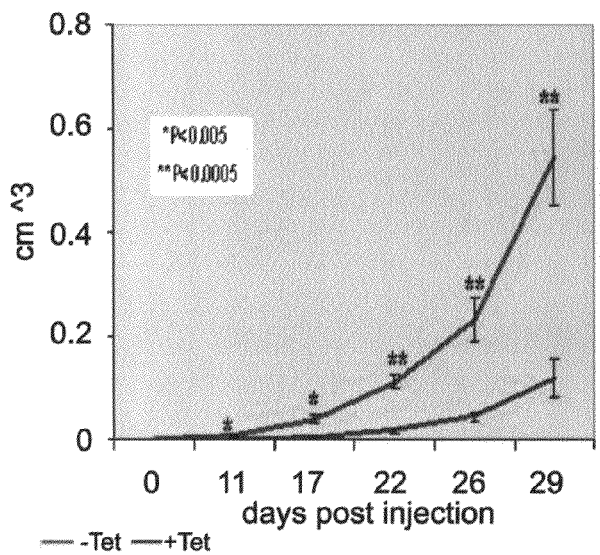
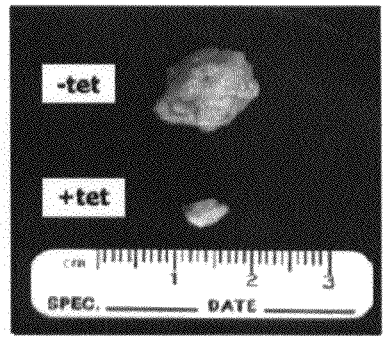
Fig. 12b
Fig. 12a
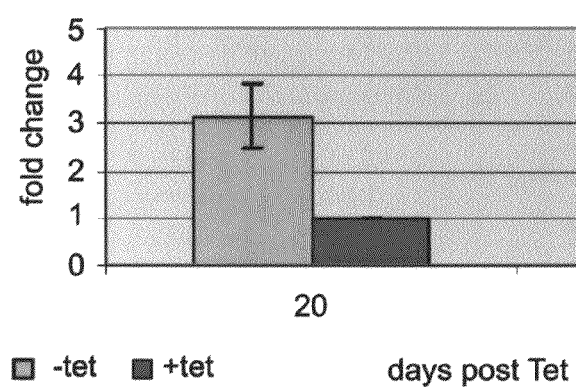
Fig. 13a
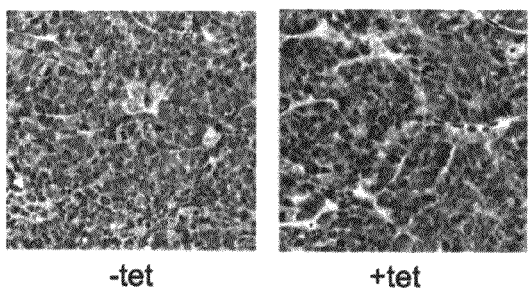
Fig. 13b   Fig. 13c

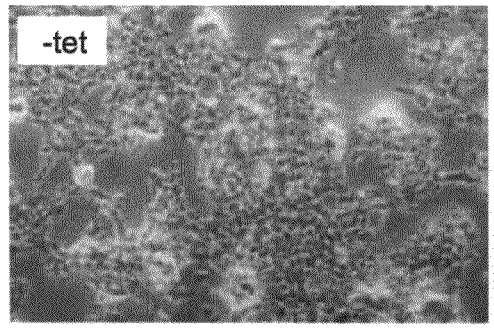 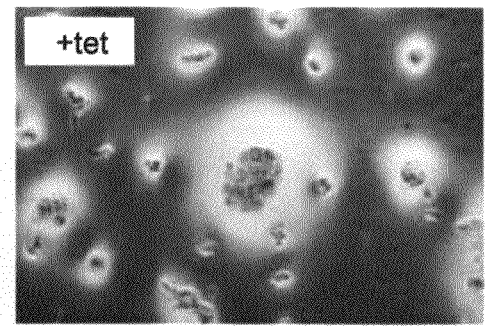
Fig. 17a    Fig. 17b
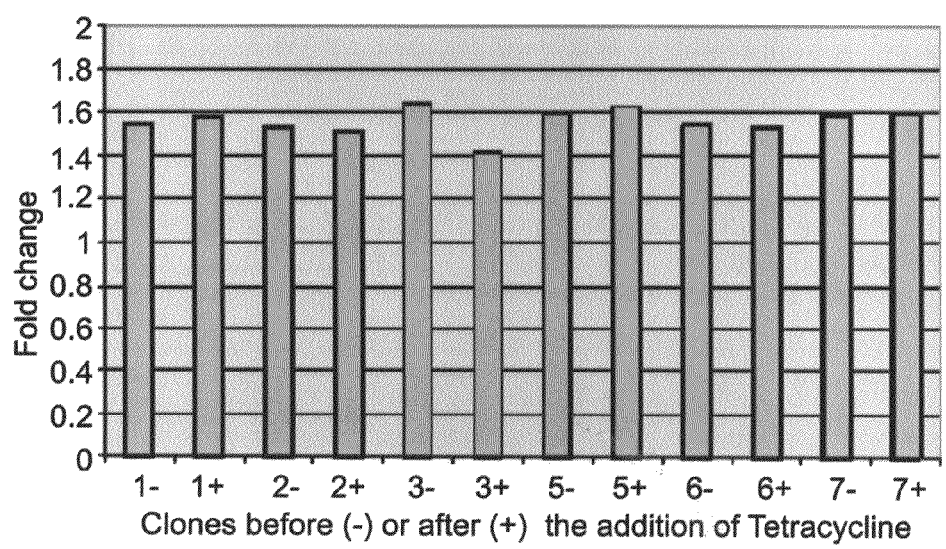
Fig. 17c

SEQUENCE LISTING

```
<160> NUMBER OF SEQ ID NOS: 23

<210> SEQ ID NO 1
<211> LENGTH: 19
<212> TYPE: DNA
<213> ORGANISM: Artificial sequence
<220> FEATURE:
<223> OTHER INFORMATION: Sequence corresponding to nucleotides 624-642
      of the human SIL gene, used as shRNA/siRNA sense strand

<400> SEQUENCE: 1
ggttctctga cagcagacg                                                    19

<210> SEQ ID NO 2
<211> LENGTH: 21
<212> TYPE: DNA
<213> ORGANISM: Artificial sequence
<220> FEATURE:
<223> OTHER INFORMATION: Sequence corresponding to nucleotides 2643-2663
``` of the human SIL gene, used as shRNA/siRNA sense strand

<400> SEQUENCE: 2
aagacaactg ctgttgaaga c                                                    21

<210> SEQ ID NO 3
<211> LENGTH: 68
<212> TYPE: DNA
<213> ORGANISM: Artificial sequence
<220> FEATURE:
<223> OTHER INFORMATION: Single strand DNA oligonucleotide

<400> SEQUENCE: 3
gatccccaag acaactgctg ttgaagactt caagagagtc ttcaacagca gttgtctttt         60
tttggaaa                                                                  68

<210> SEQ ID NO 4
<211> LENGTH: 68
<212> TYPE: DNA
<213> ORGANISM: Artificial sequence
<220> FEATURE:
<223> OTHER INFORMATION: Single strand DNA oligonucleotide

<400> SEQUENCE: 4
agctttccaa aaaaagaca actgctgttg aagactctct tgaagtcttc aacagcagtt         60
gtcttggg                                                                  68

<210> SEQ ID NO 5
<211> LENGTH: 1287
<212> TYPE: PRT
<213> ORGANISM: Homo sapiens

<400> SEQUENCE: 5

Met Glu Pro Ile Tyr Pro Phe Ala Arg Pro Gln Met Asn Thr Arg Phe
1               5                   10                  15

Pro Ser Ser Arg Met Val Pro Phe His Phe Pro Pro Ser Lys Cys Ala
            20                  25                  30

Leu Trp Asn Pro Thr Pro Thr Gly Asp Phe Ile Tyr Leu His Leu Ser
        35                  40                  45

Tyr Tyr Arg Asn Pro Lys Leu Val Val Thr Glu Lys Thr Ile Arg Leu
    50                  55                  60

Ala Tyr Arg His Ala Asn Glu Asn Lys Lys Asn Ser Ser Cys Phe Leu
65                  70                  75                  80

Leu Gly Ser Leu Thr Ala Asp Glu Asp Glu Gly Val Thr Leu Thr
            85                  90                  95

Val Asp Arg Phe Asp Pro Gly Arg Glu Val Pro Glu Cys Leu Glu Ile
            100                 105                 110

Thr Pro Thr Ala Ser Leu Pro Gly Asp Phe Leu Ile Pro Cys Lys Val
        115                 120                 125

His Thr Gln Glu Leu Cys Ser Arg Glu Met Ile Val His Ser Val Asp
    130                 135                 140

Asp Phe Ser Ser Ala Leu Lys Ala Leu Gln Cys His Ile Cys Ser Lys
145                 150                 155                 160

Asp Ser Leu Asp Cys Gly Lys Leu Leu Ser Leu Arg Val His Ile Thr
                165                 170                 175

Ser Arg Glu Ser Leu Asp Ser Val Glu Phe Asp Leu His Trp Ala Ala
            180                 185                 190

Val Thr Leu Ala Asn Asn Phe Lys Cys Thr Pro Val Lys Pro Ile Pro

```
              195                 200                 205
Ile Ile Pro Thr Ala Leu Ala Arg Asn Leu Ser Ser Asn Leu Asn Ile
210                 215                 220

Ser Gln Val Gln Gly Thr Tyr Lys Tyr Gly Tyr Leu Thr Met Asp Glu
225                 230                 235                 240

Thr Arg Lys Leu Leu Leu Leu Glu Ser Asp Pro Lys Val Tyr Ser
                245                 250                 255

Leu Pro Leu Val Gly Ile Trp Leu Ser Gly Ile Thr His Ile Tyr Ser
                260                 265                 270

Pro Gln Val Trp Ala Cys Cys Leu Arg Tyr Ile Phe Asn Ser Ser Val
                275                 280                 285

Gln Glu Arg Val Phe Ser Glu Ser Gly Asn Phe Ile Ile Val Leu Tyr
290                 295                 300

Ser Met Thr His Lys Glu Pro Glu Phe Tyr Glu Cys Phe Pro Cys Asp
305                 310                 315                 320

Gly Lys Ile Pro Asp Phe Arg Phe Gln Leu Leu Thr Ser Lys Glu Thr
                325                 330                 335

Leu His Leu Phe Lys Asn Val Glu Pro Pro Asp Lys Asn Pro Ile Arg
                340                 345                 350

Cys Glu Leu Ser Ala Glu Ser Gln Asn Ala Glu Thr Glu Phe Phe Ser
                355                 360                 365

Lys Ala Ser Lys Asn Phe Ser Ile Lys Arg Ser Ser Gln Lys Leu Ser
370                 375                 380

Ser Gly Lys Met Pro Ile His Asp His Asp Ser Gly Val Glu Asp Glu
385                 390                 395                 400

Asp Phe Ser Pro Arg Pro Ile Pro Ser Pro His Pro Val Ser Gln Lys
                405                 410                 415

Ile Ser Lys Ile Gln Pro Ser Val Pro Glu Leu Ser Leu Val Leu Asp
                420                 425                 430

Gly Asn Phe Ile Glu Ser Asn Pro Leu Pro Thr Pro Leu Glu Met Val
                435                 440                 445

Asn Asn Glu Asn Pro Pro Leu Ile Asn His Leu Glu His Leu Lys Pro
450                 455                 460

Leu Gln Pro Gln Leu Tyr Asp Glu Lys His Ser Pro Glu Val Glu Ala
465                 470                 475                 480

Gly Glu Pro Ser Leu Arg Gly Ile Pro Asn Gln Leu Asn Gln Asp Lys
                485                 490                 495

Pro Ala Leu Leu Arg His Cys Lys Val Arg Gln Pro Ala Tyr Lys
                500                 505                 510

Lys Gly Asn Pro His Thr Arg Asn Ser Ile Lys Pro Ser Ser His Asn
                515                 520                 525

Gly Pro Ser His Asp Ile Phe Glu Lys Leu Gln Thr Val Ser Ala Gly
                530                 535                 540

Asn Val Gln Asn Glu Glu Tyr Pro Ile Arg Pro Ser Thr Leu Asn Ser
545                 550                 555                 560

Arg Gln Ser Ser Leu Ala Pro Gln Ser Gln Pro His Asp Phe Val Phe
                565                 570                 575

Ser Pro His Asn Ser Gly Arg Pro Met Glu Leu Gln Ile Pro Thr Pro
                580                 585                 590

Pro Leu Pro Ser Tyr Cys Ser Thr Asn Val Cys Arg Cys Cys Gln His
                595                 600                 605

His Ser His Ile Gln Tyr Ser Pro Leu Asn Ser Trp Gln Gly Ala Asn
                610                 615                 620
```

-continued

Thr Val Gly Ser Ile Gln Asp Val Gln Ser Glu Ala Leu Gln Lys His
625                 630                 635                 640

Ser Leu Phe His Pro Ser Gly Cys Pro Ala Leu Tyr Cys Asn Ala Phe
            645                 650                 655

Cys Ser Ser Ser Pro Ile Ala Leu Arg Pro Gln Gly Asp Met Gly
                660                 665                 670

Ser Cys Ser Pro His Ser Asn Ile Glu Pro Ser Pro Val Ala Arg Pro
        675                 680                 685

Pro Ser His Met Asp Leu Cys Asn Pro Gln Pro Cys Thr Val Cys Met
690                 695                 700

His Thr Pro Lys Thr Glu Ser Asp Asn Gly Met Met Gly Leu Ser Pro
705                 710                 715                 720

Asp Ala Tyr Arg Phe Leu Thr Glu Gln Asp Arg Gln Leu Arg Leu Leu
                725                 730                 735

Gln Ala Gln Ile Gln Arg Leu Leu Glu Ala Gln Ser Leu Met Pro Cys
            740                 745                 750

Ser Pro Lys Thr Thr Ala Val Glu Asp Thr Val Gln Ala Gly Arg Gln
        755                 760                 765

Met Glu Leu Val Ser Val Glu Ala Gln Ser Ser Pro Gly Leu His Met
770                 775                 780

Arg Lys Gly Val Ser Ile Ala Val Ser Thr Gly Ala Ser Leu Phe Trp
785                 790                 795                 800

Asn Ala Ala Gly Glu Asp Gln Glu Pro Asp Ser Gln Met Lys Gln Asp
                805                 810                 815

Asp Thr Lys Ile Ser Ser Glu Asp Met Asn Phe Ser Val Asp Ile Asn
            820                 825                 830

Asn Glu Val Thr Ser Leu Pro Gly Ser Ala Ser Ser Leu Lys Ala Val
        835                 840                 845

Asp Ile Pro Ser Phe Glu Glu Ser Asn Ile Ala Val Glu Glu Glu Phe
850                 855                 860

Asn Gln Pro Leu Ser Val Ser Asn Ser Ser Leu Val Val Arg Lys Glu
865                 870                 875                 880

Pro Asp Val Pro Val Phe Phe Pro Ser Gly Gln Leu Ala Glu Ser Val
                885                 890                 895

Ser Met Cys Leu Gln Thr Gly Pro Thr Gly Gly Ala Ser Asn Asn Ser
            900                 905                 910

Glu Thr Ser Glu Glu Pro Lys Ile Glu His Val Met Gln Pro Leu Leu
        915                 920                 925

His Gln Pro Ser Asp Asn Gln Lys Ile Tyr Gln Asp Leu Leu Gly Gln
930                 935                 940

Val Asn His Leu Leu Asn Ser Ser Lys Glu Thr Glu Gln Pro Ser
945                 950                 955                 960

Thr Lys Ala Val Ile Ile Ser His Glu Cys Thr Arg Thr Gln Asn Val
                965                 970                 975

Tyr His Thr Lys Lys Thr His Ser Arg Leu Val Asp Lys Asp
            980                 985                 990

Cys Val Leu Asn Ala Thr Leu Lys Gln Leu Arg Ser Leu Gly Val Lys
        995                 1000                1005

Ile Asp Ser Pro Thr Lys Val Lys Lys Asn Ala His Asn Val Asp
        1010                1015                1020

His Ala Ser Val Leu Ala Cys Ile Ser Pro Glu Ala Val Ile Ser
        1025                1030                1035

Gly Leu Asn Cys Met Ser Phe Ala Asn Val Gly Met Ser Gly Leu
    1040                1045                1050

Ser Pro Asn Gly Val Asp Leu Ser Met Glu Ala Asn Ala Ile Ala
    1055                1060                1065

Leu Lys Tyr Leu Asn Glu Asn Gln Leu Ser Gln Leu Ser Val Thr
    1070                1075                1080

Arg Ser Asn Gln Asn Asn Cys Asp Pro Phe Ser Leu Leu His Ile
    1085                1090                1095

Asn Thr Asp Arg Ser Thr Val Gly Leu Ser Leu Ile Ser Pro Asn
    1100                1105                1110

Asn Met Ser Phe Ala Thr Lys Lys Tyr Met Lys Arg Tyr Gly Leu
    1115                1120                1125

Leu Gln Ser Ser Asp Asn Ser Glu Asp Glu Glu Pro Pro Asp
    1130                1135                1140

Asn Ala Asp Ser Lys Ser Glu Tyr Leu Leu Asn Gln Asn Leu Arg
    1145                1150                1155

Ser Ile Pro Glu Gln Leu Gly Gly Gln Lys Glu Pro Ser Lys Asn
    1160                1165                1170

Asp His Glu Ile Ile Asn Cys Ser Asn Cys Glu Ser Val Gly Thr
    1175                1180                1185

Asn Ala Asp Thr Pro Val Leu Arg Asn Ile Thr Asn Glu Val Leu
    1190                1195                1200

Gln Thr Lys Ala Lys Gln Gln Leu Thr Glu Lys Pro Ala Phe Leu
    1205                1210                1215

Val Lys Asn Leu Lys Pro Ser Pro Ala Val Asn Leu Arg Thr Gly
    1220                1225                1230

Lys Ala Glu Phe Thr Gln His Pro Glu Lys Glu Asn Glu Gly Asp
    1235                1240                1245

Ile Thr Ile Phe Pro Glu Ser Leu Gln Pro Ser Glu Thr Leu Lys
    1250                1255                1260

Gln Met Asn Ser Met Asn Ser Val Gly Thr Phe Leu Asp Val Lys
    1265                1270                1275

Arg Leu Arg Gln Leu Pro Lys Leu Phe
    1280                1285

<210> SEQ ID NO 6
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 6
gactacttca ggcacagatt c                                              21

<210> SEQ ID NO 7
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 7
atgcatgcca acacactg                                                  18

<210> SEQ ID NO 8
<211> LENGTH: 20
<212> TYPE: DNA

-continued

<213> ORGANISM: Artificial sequence
<220> FEATURE:
<223> OTHER INFORMATION: Single strand DNA oligonucleotide

<400> SEQUENCE: 8
ccgcagttct ccaagaagac                                           20

<210> SEQ ID NO 9
<211> LENGTH: 17
<212> TYPE: DNA
<213> ORGANISM: Artificial sequence
<220> FEATURE:
<223> OTHER INFORMATION: Single strand DNA oligonucleotide

<400> SEQUENCE: 9
gaactgaggc ggcaaac                                              17

<210> SEQ ID NO 10
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 10
gagacactgc aaagtaagac ag                                        22

<210> SEQ ID NO 11
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 11
gtggagggtc ttataggata ctc                                       23

<210> SEQ ID NO 12
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 12
ccaagtctgc ccagaaagct c                                         21

<210> SEQ ID NO 13
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 13
ggaatggtga caacatgctg g                                         21

<210> SEQ ID NO 14
<211> LENGTH: 25
<212> TYPE: RNA
<213> ORGANISM: Artificial sequence
<220> FEATURE:
<223> OTHER INFORMATION: SIL stealth 1207

<400> SEQUENCE: 14
gggcuugcug uuugcgauac auauu                                     25

```
<210> SEQ ID NO 15
<211> LENGTH: 25
<212> TYPE: RNA
<213> ORGANISM: Artificial sequence
<220> FEATURE:
<223> OTHER INFORMATION: SIL stealth 2163

<400> SEQUENCE: 15
ccaucuuacu guuccacaaa cguuu                                        25

<210> SEQ ID NO 16
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 16
atgcatatcg gttcctcaca ga                                           22

<210> SEQ ID NO 17
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 17
actccatttg tcttccagct tg                                           22

<210> SEQ ID NO 18
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 18
ctcctggatt ctgctggctg a                                            21

<210> SEQ ID NO 19
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 19
ggatgctgcc tggagtgtg                                               19

<210> SEQ ID NO 20
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 20
agggctcaca gctcgaagaa c                                            21

<210> SEQ ID NO 21
<211> LENGTH: 22
<212> TYPE: DNA
<213> ORGANISM: Artificial sequence
<220> FEATURE:
```

```
<223> OTHER INFORMATION: Single strand DNA oligonucleotide

<400> SEQUENCE: 21
ttgatagcaa agctcttgcc tg                                          22

<210> SEQ ID NO 22
<211> LENGTH: 19
<212> TYPE: DNA
<213> ORGANISM: Artificial sequence
<220> FEATURE:
<223> OTHER INFORMATION: Sequence corresponding to nucleotides 861-879
      of human E2F1 gene, used as shRNA/siRNA sense strand

<400> SEQUENCE: 22
gacgtgtcag gaccttcgt                                              19

<210> SEQ ID NO 23
<211> LENGTH: 19
<212> TYPE: RNA
<213> ORGANISM: Artificial sequence
<220> FEATURE:
<223> OTHER INFORMATION: Scrambled SIL siRNA

<400> SEQUENCE: 23
acugcgcuac caucgugcc                                              19
```

PHARMACEUTICAL COMPOSITION AND METHOD FOR REGULATING ABNORMAL CELLULAR PROLIFERATION

RELATED APPLICATIONS

This Application is a National Phase of PCT Patent Application No. PCT/IL2006/001324 having International filing date of Nov. 16, 2006, which claims the benefit of U.S. Provisional Patent Application No. 60/737,384 filed on Nov. 17, 2005. The contents of the above Applications are all incorporated herein by reference.

FIELD AND BACKGROUND OF THE INVENTION

The present invention relates to pharmaceutical compositions and methods for regulating abnormal cell proliferation. More particularly, the present invention relates to pharmaceutical compositions and methods of treating diseases which are associated with pathologically hyperproliferating cells, such as tumors/cancers.

Diseases associated with abnormal cell proliferation, comprise numerous diseases of major clinical and economic impact for which no satisfactory treatment methods are available. Such diseases comprise those associated with pathological cellular hyperproliferation—notably malignant diseases—as well as benign tumors, pre-cancers, hyperplasias, polyps, warts, growths and the like; and autoimmune diseases characterized by hyperproliferating clones of autoreactive lymphocytes. Diseases associated with abnormal proliferation also comprise those conversely associated with pathological cellular hypoproliferation such as degenerative disorders, Alzheimer's disease, Parkinson's disease, amyotrophic lateral sclerosis (ALS), retinitis pigmentosa, and osteoporosis. Natural senescence and undesirable senescence-related phenomena such as wrinkling can also be considered as being degenerative disorders associated with cellular hypoproliferation.

Colon cancer, which is also known as cancer of the large bowel and colorectal cancer, is second only to lung cancer as a cause of cancer death in the United States. Colorectal cancer is a common malignant condition that generally occurs in individuals 50 years of age or older; and the overall incidence rate of colon cancer has not changed substantially during the past 40 years (Harrison's Principles of Internal Medicine, 14/e, McGraw-Hill Companies, New York, 1998). In 1999, 129,400 new cases of colorectal cancer were estimated in the United States, resulting in 56,600 deaths therefrom. The cumulative lifetime risk for the disease is 1 in 20. The strongest risk factor for colon cancer is age, with the incidence rates rising from 10 per 100,000 at age 40-45 to 300 per 100,000 at age 75-80. Men are more likely to develop colon cancer than women; black Americans are more likely than white Americans to be diagnosed with colorectal cancer; and smokers, drinkers, sedentary, and obese persons are more likely to develop colon cancer. The treatment of colon cancer once diagnosis is made depends on the extent of the cancer's invasion of the colon tissue, lymph nodes, and metastasis to other organs such as the liver. Surgery is the primary treatment and results in cure in approximately 50 percent of patients. However, recurrence following surgery is a major problem and often is the ultimate cause of death.

Cancer of the uterine cervix is one of the most common malignancies in women and remains a significant public health problem throughout the world. In the United States alone, invasive cervical cancer accounts for approximately 19 percent of all gynecological cancers (Miller et al. (1993) in "Surveillance Epidemiology, and End Results Program cancer Statistics Review: 1973-1990", NIH Pub. No. 93-2789, Bethesda, Md.: National Cancer Institute). For example, in 1996, it is estimated that there Were 14,700 newly diagnosed cases and 4900 deaths attributed to this disease (American Cancer Society, Cancer Facts & Figures 1996, Atlanta, Ga.: American Cancer Society, 1996). In many developing countries, where mass screening programs are not widely available, the clinical problem is more serious. Worldwide, the number of new cases is estimated to be 471,000 with a 4-year survival rate of 40 percent (Munoz et al. (1989) "Epidemiology of Cervical Cancer" in "Human Papillomavirus", New York, Oxford Press, pp 9-39; and National Institutes of Health, Consensus Development Conference Statement on Cervical Cancer, Apr. 1-3, 1996).

There is therefore clearly a long-felt and urgent need. for novel, safe and effective pharmacological agents which can modulate cell proliferation so as to treat diseases associated with abnormal cellular proliferation, such as tumors, for example colon cancer and cervical cancer.

Standard chemotherapeutic agents employed for treating various types of malignancies notably include those which target and block mitosis, such as Vinca alkaloids such as vincristine, taxol and related compounds. Some of these drugs are also used in non-neoplastic conditions; for example, colchicine in familial Mediterranean fever and gout, vincristine in autoimmune thrombocytopenia, etc. Remarkably, although mitosis is a normal process shared by all proliferating cells, anti-mitotic drugs can have an excellent therapeutic ratio with relatively few harmful side effects. It appears that cancer cells have a unique sensitivity to anti-mitotic drugs. Therefore there is an extensive effort in developing other drugs that target proteins regulating mitosis. Some (e.g. UCN01) are currently in clinical trials (Jordan, M. A. and L. Wilson, 2004. Nat Rev Cancer 4: 253-65; Keen, N. and S. Taylor, 2004. Nat Rev Cancer 4: 927-36; Sikorska, A. et al., 2004. Clin Lab Haematol 26: 407-11; Cerquaglia, C. et al., 2005. Cliff Drug Targets Inflamm Allergy 4: 117-24; Fuse, E. et al., 2005. J Clin Pharmacol 45: 394-403).

The mitosis regulatory protein SIL is a protein which is tightly regulated during the cell cycle and whose expression is limited to proliferating cells. Its mRNA expression is higher in rapidly proliferating cells and tissues, and it decreases rapidly during terminal differentiation. Upon entrance of arrested G0 cells into the cell cycle SIL is induced in an immediate early fashion. The SIL protein accumulates, reaches peak levels in mitosis and then degrades upon entrance to the next cell cycle (Izraeli, S. et al., 1997. Cell Growth Differ 8: 1171-9).

The SIL gene [stem cell leukemia (SCL) interrupting locus, also termed as STIL (SCL/TAL1 interrupting locus)], located on chromosome 1, was cloned from the most common chromosomal rearrangement in T-cell acute lymphoblastic leukemia (ALL). In this rearrangement, the coding region of SIL is deleted and its promoter assumes control of a downstream gene, SCL. The resulting aberrant expression of SCL leads to the development of leukemia (Aplan, P. et al., 1991. Mol Cell Biol 11: 5462-9). The human SIL gene encodes a large cytosolic protein of 150 kilodaltons composed of 1287 amino acid residues that has been found to be highly conserved in the mouse and zebrafish (Collazo-Garcia, N. et al., 1995. Genomics 30: 506-513; Golling, G. et al., 2002. Nat Genet 31: 135-40). The importance of SIL to cell growth and differentiation was also shown in a knockout mouse, which carried a null mutation of the Sil gene (Izraeli, S. et al., 1999. Nature 399: 691-4). Mice lacking the gene, die at mid-gestation, they manifest striking developmental defects in the midline and left/right body axis, and the most anterior end of the developing brain is not separated, resulting in holoprosencephaly (cyclopia), with the rest of the neural tube being apoptotic. Left/right asymmetry axis is randomized. SIL is not absolutely required for survival of normal cells as mouse embryonic stem cells lacking SIL proliferate normally and grow teratomas in nude mice that are indistinguishable from those formed by normal embryonic stem cells (Izraeli, S. et al., 1999. Nature 399: 691-4). Detailed analysis of the SIL knockout mice and additional genetic experiments suggest that SIL is required for the response to Hedgehog signaling (Izraeli, S. et al., 1999. Nature 399: 691-4; Izraeli, S. et al., 2001. Genesis 31: 72-7). However, it is still unclear if SIL participates in the biochemical signaling cascade induced by stimulation by Hedgehog proteins.

The critical requirement of SIL for cell growth, proliferation and survival during embryonic development, and its regulation during the cell cycle prompted the hypothesis that SIL might have a role in tumorigenesis. SIL has been found by the present inventors, and others, to be ubiquitously expressed in cancer and to characterize tumors with increased mitotic fraction (Aplan, P. et al., 1991. Mol Cell Biol 11: 5462-9; Izraeli, S. et al., 1997. Cell Growth Differ 8: 1171-9; Erez, A. et al., 2004. Oncogene 23: 5371-7). SIL was shown to be expressed by RNA and protein analysis in multiple types of cancer cells (tissues and cell lines), the only exception being gliomas where the expression of SIL is low. In contrast, in primary normal tissues it is expressed mainly in bone marrow, thymus, and testis. In non dividing tissues SIL expression is extremely low (Izraeli, S. et al., 1997. Cell Growth Differ 8: 1171-9). Publicly available microarray data describes patterns of SIL expression (see, for example, http://expression.gnf.org/cgi-bin/index.cgi#Q). Examples of cancers in which SIL has been shown to be overexpressed include primary cells and cell lines of acute lymphoblastic leukemia (ALL), acute myeloid leukemias (AML), chronic myeloid leukemia (CML), Burkitt's lymphoma, non-Hodgkin's lymphoma. Other types of cancers in which SIL has been shown to be overexpressed include primary cells and cell lines of lung cancer (both small and non-small cell lung cancer), colon cancer, breast cancer, prostate cancer, melanoma, cervical cancer, liver cancer, and teratocarcinoma. Immunohistochemical staining experiments have revealed high expression of SIL in up to a third of specimens tested for each of multiple types of cancer. The pattern of SIL expression has been studied in detail in lung cancer. Tumors highly expressing SIL had a higher mitotic index and a higher expression of other mitotic regulators (Erez, A. et al., 2004. Oncogene 23: 5371-7). These findings and others suggest that SIL expression characterizes a subset of more aggressive tumors with a higher mitotic fraction, and have found SIL to be one of the predictive genes for metastatic disease in adenocarcinomas of different tissues (Ramaswamy, S. et al., 2003. Nat Genet 33: 49-54). SIL protein expression correlates with the expression of mitotic checkpoint genes and with the mitotic index of the tumors, in itself a bad prognostic sign. Thus, overexpression of SIL is common in cancers and is associated with increased mitotic index, metastatic spread and consequently worse prognosis.

While, as described above, prior art anti-mitotic drugs can be used for treatment of diseases associated with pathological cellular hyperproliferation, such as cancer, such drugs nevertheless remain of limited effectiveness and are associated with harmful side-effects, for example towards healthy cells as a result of systemic drug administration.

Thus, the prior art fails to provide an adequate method of treating diseases associated with abnormal cellular proliferation, such as tumors/cancers.

There is thus a widely recognized need for, and it would be highly advantageous to have, a method devoid of the above limitation.

SUMMARY OF THE INVENTION

The present invention discloses the use of SIL activity/level modulation, including cell-specific modulation, for regulating the growth of abnormally proliferating cells, and further discloses novel pharmaceutical compositions for achieving such modulation. In particular, the present invention discloses the use of SIL activity/level modulation for the treatment of diseases associated with abnormally proliferating cell populations, such as tumors/cancers. This use can be effected in a variety of ways as further described and exemplified hereinbelow.

According to one aspect of the present invention there is provided a method of treating a disease associated with a cell population which proliferates abnormally in a subject, the method comprising administering to the subject a therapeutically effective amount of at least one modulator capable of modulating in the cell population a level and/or activity of a polypeptide having an amino acid sequence at least 60 percent similar to SEQ ID NO: 5, as determined using the Standard protein-protein BLAST [blastp] software of the NCBI, thereby regulating proliferation of the cell population for treating the disease in the subject.

According to further features in preferred embodiments of the invention described below, the amino acid sequence is at least 95 percent similar to SEQ ID NO: 5, as determined using the Standard protein-protein BLAST [blastp] software of the NCBI.

According to still further features in the described preferred embodiments, the amino acid sequence is as set forth in SEQ ID NO: 5.

According to still further features in preferred embodiments, modulating the level and/or activity of the polypeptide is decreasing or eliminating the level and/or activity of the polypeptide, and whereas the at least one modulator is selected from the group consisting of: (a) a molecule capable of binding the polypeptide; (b) an enzyme capable of cleaving the polypeptide; (c) an siRNA molecule capable of inducing degradation of an mRNA encoding the polypeptide; (d) a DNAzyme capable of cleaving an mRNA or DNA encoding the polypeptide; (e) an antisense polynucleotide capable of hybridizing with an mRNA encoding the polypeptide; and (f) a ribozyme capable of cleaving an mRNA encoding the polypeptide.

According to still further features in the described preferred embodiments, the siRNA molecule has a sense strand corresponding to a nucleotide sequence which comprises SEQ ID NO: 1, 2, 14 and/or 15.

According to still further features in the described preferred embodiments, administering the at least one modulator to the subject is effected by administering to the subject at least one nucleic acid construct which comprises at least one polynucleotide encoding the at least one modulator.

According to still further features in the described preferred embodiments, the disease is a tumor.

According to still further features in the described preferred embodiments, the disease is a malignancy.

According to still further features in the described preferred embodiments, the disease is an inflammatory proliferative disorder.

According to still further features in the described preferred embodiments, the disease is selected from the group consisting of a gastrointestinal disease, a uterine disease, a glandular disease, a pulmonary disease, and a neurological disease.

According to still further features in the described preferred embodiments, the disease is selected from the group consisting of a colorectal disease, a uterine cervical disease, a pancreatic disease, a mammary disease, a prostate disease, a pulmonary epithelial disease and a glial disease.

According to another aspect of the present invention there is provided a method of regulating proliferation of a cell population which proliferates abnormally, the method comprising contacting the cell population with a modulator capable of modulating in the cell population a level and/or activity of a polypeptide having an amino acid sequence at least 60 percent similar to SEQ ID NO: 5, as determined using the Standard protein-protein BLAST [blastp] software of the NCBI, thereby regulating proliferation of the cell population.

According to further features in preferred embodiments of the invention described below, the amino acid sequence is at least 95 percent similar to SEQ ID NO: 5, as determined using the Standard protein-protein BLAST [blastp] software of the NCBI.

According to still further features in the described preferred embodiments, the amino acid sequence is as set forth in SEQ ID NO: 5.

According to still further features in preferred embodiments, modulating the level and/or activity of the polypeptide is decreasing or eliminating the level and/or activity of the polypeptide, and whereas the at least one modulator is selected from the group consisting of: (a) a molecule capable of binding the polypeptide; (b) an enzyme capable of cleaving the polypeptide; (c) an siRNA molecule capable of inducing degradation of an mRNA encoding the polypeptide; (d) a DNAzyme capable of cleaving an mRNA or DNA encoding the polypeptide; (e) an antisense polynucleotide capable of hybridizing with an mRNA encoding the polypeptide; and (f) a ribozyme capable of cleaving an mRNA encoding the polypeptide.

According to still further features in the described preferred embodiments, the siRNA molecule has a sense strand corresponding to a nucleotide sequence which comprises SEQ ID NO: 1, 2, 14 or 15.

According to still further features in the described preferred embodiments, administering the at least one modulator to the cell population is effected by administering to the cell population at least one nucleic acid construct which comprises at least one polynucleotide encoding the at least one modulator.

According to still further features in the described preferred embodiments, the at least one nucleic acid construct comprises at least one transcription control sequence operatively linked to the at least one polynucleotide.

According to still further features in the described preferred embodiments, the at least one transcription control sequence is inducible.

According to still further features in the described preferred embodiments, the cell population is a tumor.

According to still further features in the described preferred embodiments, the cell population is a malignancy.

According to still further features in the described preferred embodiments, the cell population is of a lineage selected from the group consisting of a gastrointestinal lineage, a uterine lineage, a glandular lineage, a pulmonary lineage and a neurological lineage.

According to still further features in the described preferred embodiments, the cell population is of a lineage selected from the group consisting of a colorectal lineage, a uterine cervical lineage, a pancreatic lineage, a mammary lineage, a pulmonary epithelial lineage, a keratinocyte cell lineage and a glial lineage.

According to yet another aspect of the present invention there is provided a recombinant polynucleotide comprising a nucleic acid sequence which encodes and/or comprises at least one molecule capable of modulating in a cell a level and/or activity of a polypeptide having an amino acid sequence at least 60 percent similar to SEQ ID NO: 5, as determined using the Standard protein-protein BLAST [blastp] software of the NCBI.

According to still another aspect of the present invention there is provided an isolated polynucleotide comprising a nucleic acid sequence which encodes and/or comprises at least one molecule capable of down-regulating in a cell a level and/or activity of a polypeptide having an amino acid sequence at least 60 percent similar to SEQ ID NO: 5, as determined using the Standard protein-protein BLAST [blastp] software of the NCBI.

According to still further features in the described preferred embodiments, the amino acid sequence is at least 95 percent similar to SEQ ID NO: 5, as determined using the Standard protein-protein BLAST [blastp] software of the NCBI.

According to still further features in the described preferred embodiments, the amino acid sequence is as set forth in SEQ ID NO: 5.

According to an additional aspect of the present invention there is provided an isolated polynucleotide comprising a nucleic acid sequence capable of down-regulating in a cell a level and/or activity of a polypeptide having an amino acid sequence at least 95 percent similar to SEQ ID NO:5 as determined using the Standard protein-protein BLAST [blastp] software of the NCBI, wherein the nucleic acid sequence is capable of inducing apoptosis in the cell.

According to yet an additional aspect of the present invention there is provided an isolated polynucleotide comprising a nucleic acid sequence capable of down-regulating in a cell a level and/or activity of a polypeptide having an amino acid sequence as set forth in SEQ ID NO:5, wherein the nucleic acid sequence is capable of inducing apoptosis in the cell.

According to still further features in the described preferred embodiments, the at least one molecule is selected from the group consisting of: (a) a molecule capable of binding the polypeptide; (b) an enzyme capable of cleaving the polypeptide; (c) an siRNA molecule capable of inducing degradation of an mRNA encoding the polypeptide; (d) a DNAzyme capable of cleaving an mRNA or DNA encoding the polypeptide; (e) an antisense polynucleotide capable of hybridizing with an mRNA encoding the polypeptide; and (f) a ribozyme capable of cleaving an mRNA encoding the polypeptide.

According to still further features in the described preferred embodiments, the siRNA molecule has a sense strand corresponding to a nucleotide sequence which comprises SEQ ID NO: 1, 2, 14 or 15.

According to still further features in the described preferred embodiments, the nucleic acid sequence comprises an siRNA molecule, the siRNA molecule has a sense strand corresponding to a nucleotide sequence as set forth in SEQ ID NO: 2, 14 or 15.

According to further features in preferred embodiments of the invention described below, the cell is a tumor cell.

According to still further features in the described preferred embodiments, the cell is a malignant cell According to still further features in the described preferred embodiments, the cell is of a lineage selected from the group consisting of a gastrointestinal lineage, a uterine lineage, a glandular lineage, a pulmonary lineage, and a neurological lineage According to still further features in the described preferred embodiments, the cell is of a lineage selected from the group consisting of a colorectal lineage, a uterine cervical lineage, a pancreatic lineage, a mammary lineage, a pulmonary epithelial lineage, a keratinocyte cell lineage and a glial lineage.

According to still another aspect of the present invention there is provided a nucleic acid construct comprising the recombinant polynucleotide, wherein the nucleic acid construct further comprises at least one expression control sequence being operatively linked to the recombinant polynucleotide and capable of controlling expression of the recombinant polynucleotide in a host cell.

According to a further aspect of the present invention, there is provided a pharmaceutical composition for treatment of a disease associated with a cell population which proliferates abnormally in a subject, the pharmaceutical composition comprising a pharmaceutically acceptable carrier, and, as an active ingredient, the recombinant polynucleotide.

According to a further aspect of the present invention, there is provided a pharmaceutical composition for treatment of a disease associated with a cell population which proliferates abnormally in a subject, the pharmaceutical composition comprising a pharmaceutically acceptable carrier, and, as an active ingredient, the isolated polynucleotide.

According to a yet further aspect of the present invention there is provided a pharmaceutical composition for treatment of a disease associated with a cell population which proliferates abnormally in a subject, the pharmaceutical composition comprising a pharmaceutically acceptable carrier, and, as an active ingredient, the nucleic acid construct.

According to still a further aspect of the present invention there is provided a cosmetic composition for treatment of a disease associated with a cell population which proliferates abnormally in a subject, the pharmaceutical composition comprising a pharmaceutically acceptable carrier, and as an active ingredient, the isolated polynucleotide.

According to still a further aspect of the present invention there is provided a cosmetic composition for treatment of a disease associated with a cell population which proliferates abnormally in a subject, the pharmaceutical composition comprising a pharmaceutically acceptable carrier, and as an active ingredient, the nucleic acid construct.

According to a still a further aspect of the present invention there is provided an article of manufacture comprising packaging material and a pharmaceutical composition identified in print in or on the packaging material for treatment of a disease associated with a cell population which proliferates abnormally in a subject, wherein the pharmaceutical composition comprises a pharmaceutically acceptable carrier, and a therapeutically effective amount of the recombinant polynucleotide.

According to a still a further aspect of the present invention there is provided an article of manufacture comprising packaging material and a pharmaceutical composition identified in print in or on the packaging material for treatment of a disease associated with a cell population which proliferates abnormally in a subject, wherein the pharmaceutical composition comprises a pharmaceutically acceptable carrier, and a therapeutically effective amount of the isolated polynucleotide.

According to an additional aspect of the present invention there is provided an article of manufacture comprising packaging material and a pharmaceutical composition identified in print in or on the packaging material for treatment of a disease associated with a cell population which proliferates abnormally in a subject, wherein the pharmaceutical composition comprises a pharmaceutically acceptable carrier, and a therapeutically effective amount of the nucleic acid construct.

According to an additional aspect of the present invention there is provided an article of manufacture comprising packaging material and a cosmetic composition identified in print in or on the packaging material for treatment of a disease associated with a cell population which proliferates abnormally in a subject, wherein the cosmetic composition comprises a dermatologically acceptable carrier, and a therapeutically effective amount of the isolated polynucleotide.

According to an additional aspect of the present invention there is provided an article of manufacture comprising packaging material and a cosmetic composition identified in print in or on the packaging material for treatment of a disease associated with a cell population which proliferates abnormally in a subject, wherein the pharmaceutical composition comprises a dermatologically acceptable carrier, and a therapeutically effective amount of the nucleic acid construct.

According to further features in preferred embodiments of the invention described below, the at least one active ingredient is selected from the group consisting of: (a) a molecule capable of binding the polypeptide; (b) an enzyme capable of cleaving the polypeptide; (c) an siRNA molecule capable of inducing degradation of an mRNA encoding the polypeptide; (d) a DNAzyme capable of cleaving an mRNA or DNA encoding the polypeptide; (e) an antisense polynucleotide capable of hybridizing with an mRNA encoding the polypeptide; and (f) a ribozyme capable of cleaving an mRNA encoding the polypeptide.

According to still further features in the described preferred embodiments, the siRNA molecule has a sense strand corresponding to a nucleotide sequence which comprises SEQ ID NO: 1 or 2.

The present invention successfully addresses the shortcomings of the presently known configurations by providing a method of using modulation of SIL activity/levels so as to enable regulation of growth of abnormally proliferating cells, to thereby achieve treatment of diseases associated with abnormally proliferating cells, such as tumors.

According to still further features in the described preferred embodiments, the cell population is of a lineage selected from the group consisting of a gastrointestinal lineage, a uterine lineage, a glandular lineage, a pulmonary lineage, and a neurological lineage.

According to still further features in the described preferred embodiments, the cell population is of a lineage selected from the group consisting of a colorectal lineage, a uterine cervical lineage, a pancreatic lineage, a mammary lineage, a pulmonary epithelial lineage and a glial lineage.

According to still further features in the described preferred embodiments, the siRNA molecule is encoded by an expression vector which comprises SEQ ID NO:1, 2, 14 and/or 15.

According to still further features in the described preferred embodiments, the siRNA molecule is encoded by an expression vector which comprises SEQ ID NO: 2, 14 or 15.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications and other references mentioned herein are incorporated by reference in their entirety. In case of conflict, the patent specification, including definitions, will control. In addition, the materials, methods, and examples are illustrative only and not intended to be limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figure 1:
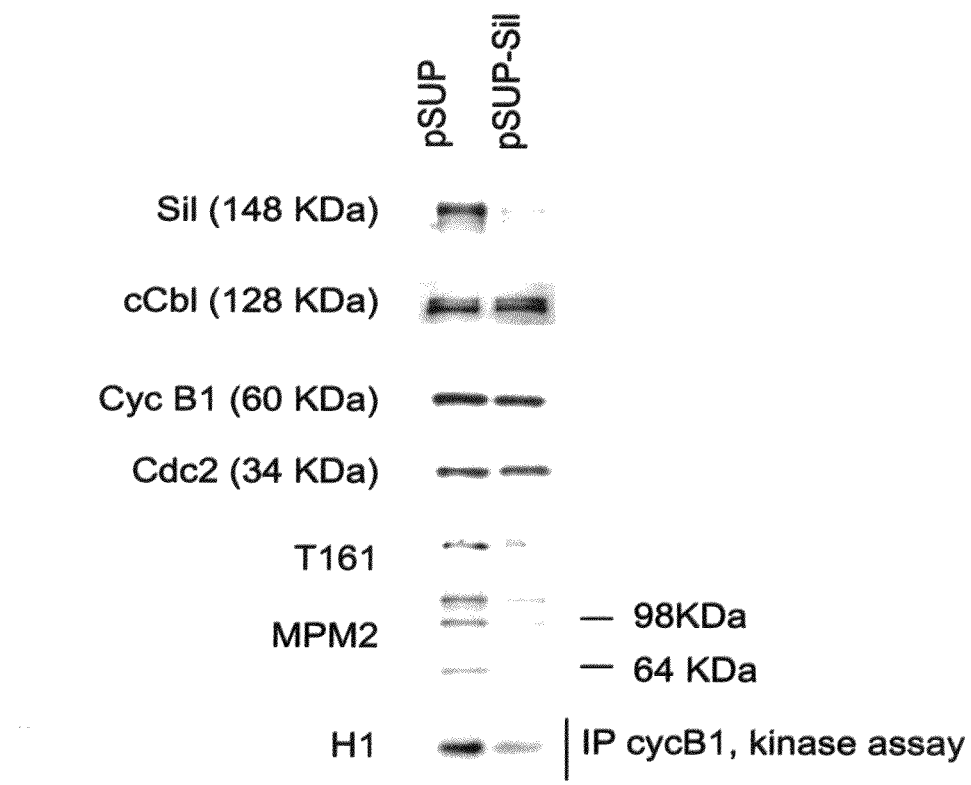
Figure 2A:
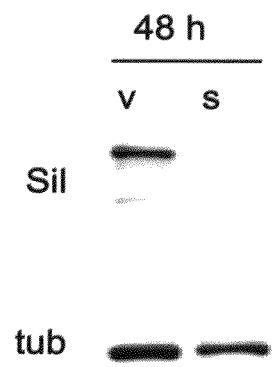
Figure 2B:
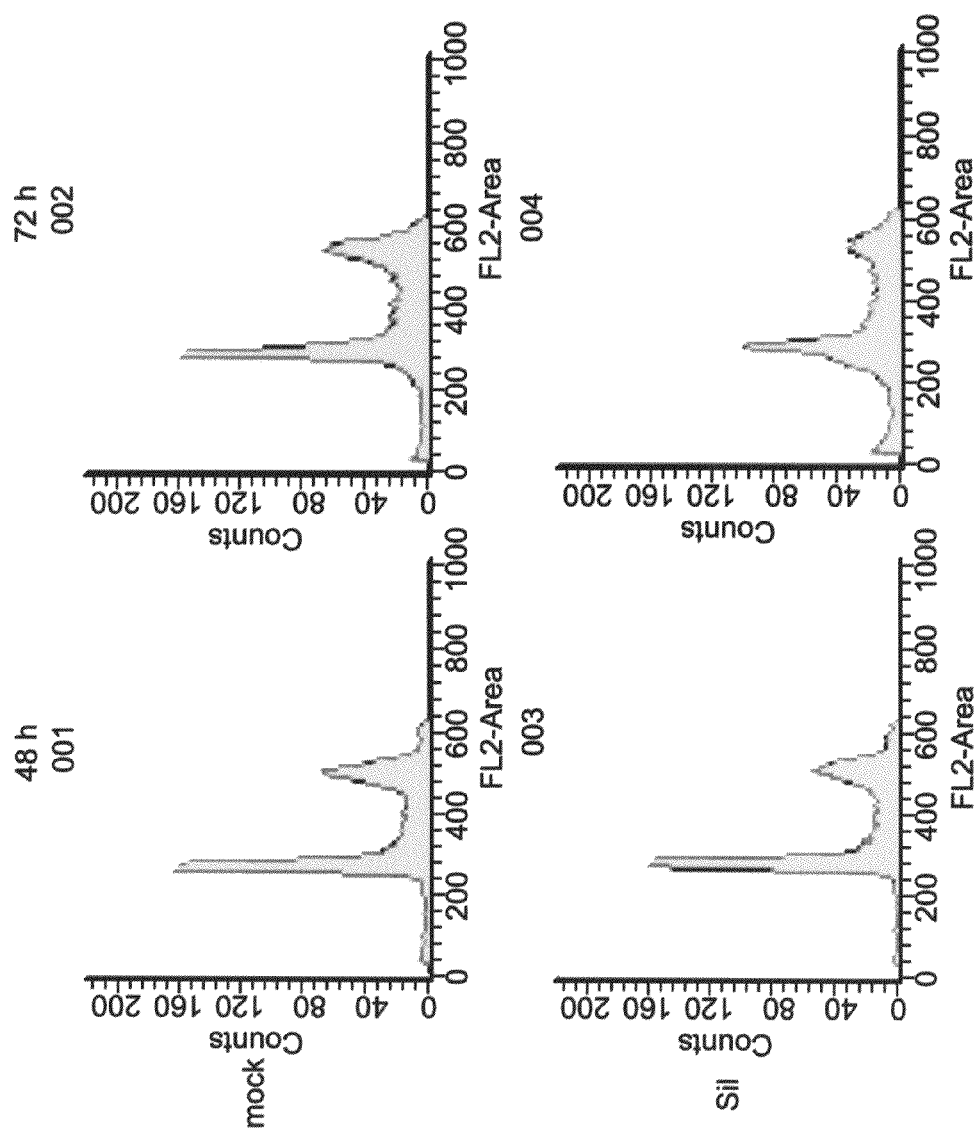
Figure 3A:
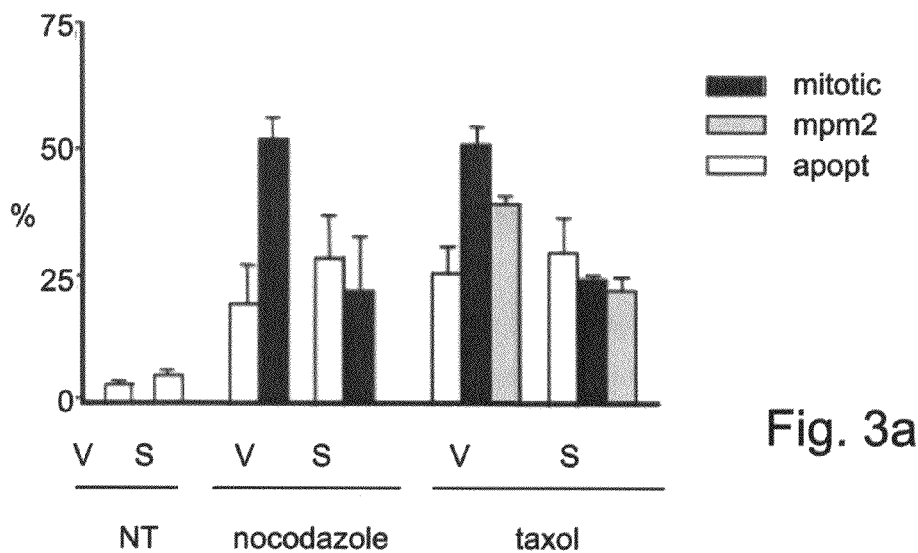
Figure 3B:
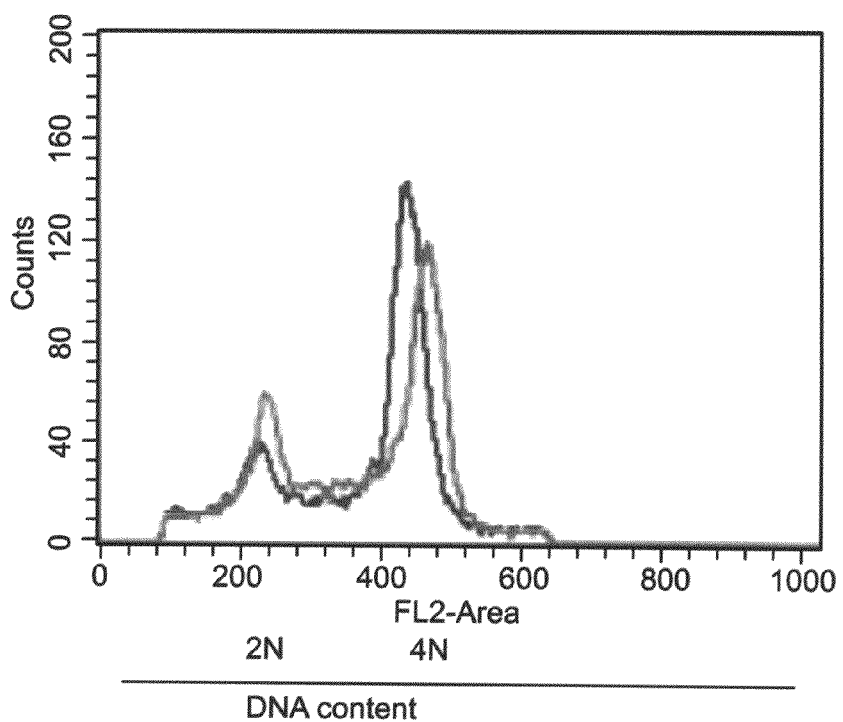
Figure 5A:
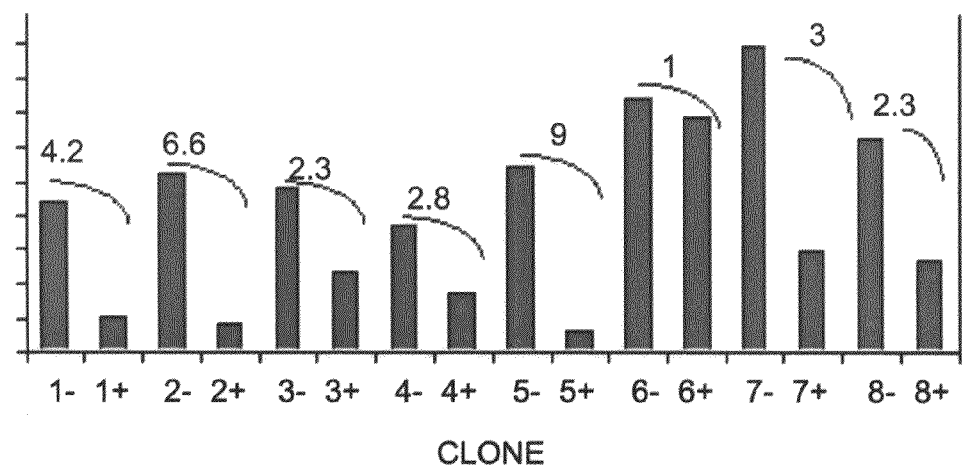
Figure 5B:
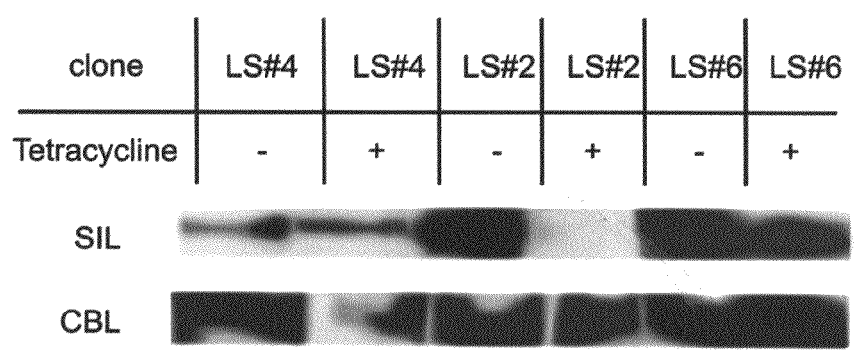
Figure 6A:
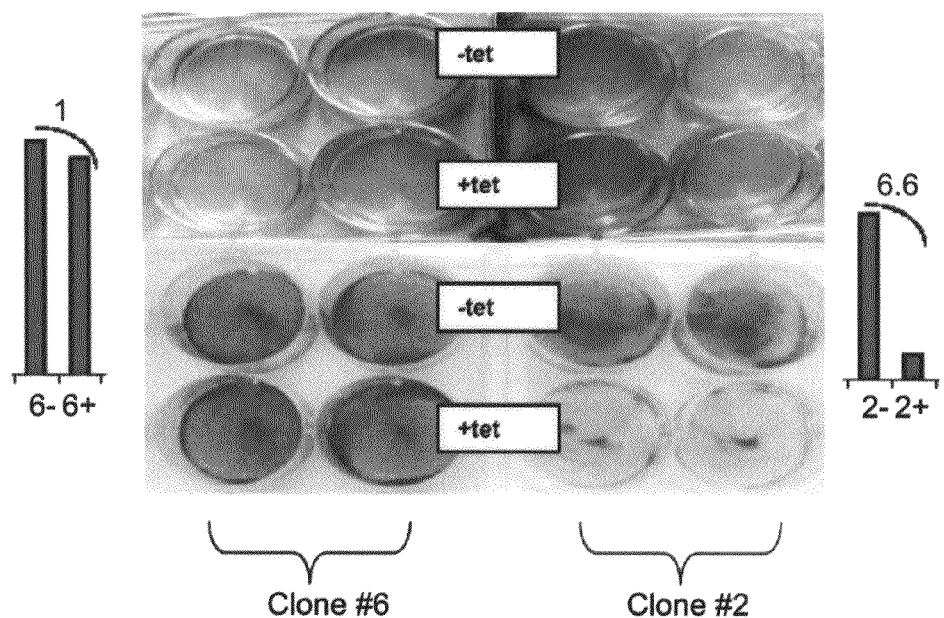
Figure 6B:
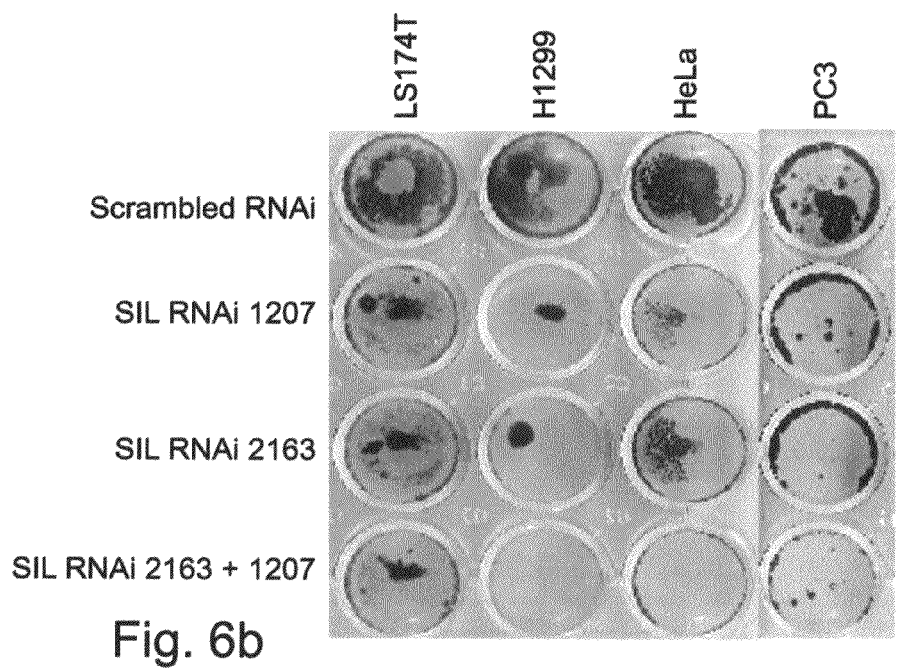

FIG. 1 depicts Western blot results showing downmodulation of SIL protein levels in HeLa cells transfected with pSUPER-Sil but not in control cells transfected with the empty vector (pSUP). Cells were transfected and after 24 hours were treated with the indicated microtubule inhibitors for 18 hours. Shown is a Western blot analysis of samples treated with taxol, stained for Sil, c-Cbl (as a loading control), cyclin B1 (Cyc B1), Cdc2, Cdc2 phosphorylation on threonine 161 (T-161), MPM2 and Cdc2/cyclin B1 kinase assay;

FIGS. 2a-b depict SIL protein expression and cell cycle profiles of HeLa cells double-transfected with pSuper (mock "V") or pSuper Sil (Sil "S") vectors along with a vector encoding GFP-H2B fusion as a transfection marker. FIG. 2a is a Western blot analysis. Tubulin (tub) was used as loading marker. FIG. 2b is a FACS analysis of cell cycle profiles of GFP positive cells analyzed at the indicated times after transfection;

FIGS. 3a-b are analyses of HeLa cells transfected with pSUPER-Sil or the empty vector. FIG. 3a is a histogram depicting the mitotic index (black bars), MPM2 staining (gray bars), and apoptotic index (white bars) of cells transfected with empty vector (V) or pSUPER-Sil (S). As a control, the apoptotic index of untreated cells (NT) is also reported. The values reported represent the mean of two independent experiments performed in duplicates. Twenty-four hours following transfection cells were treated with the indicated microtubule inhibitors for 18 hours. FIG. 3b is a FACS histogram depicting the profile of cells transfected with empty vector (blue) or pSUPER Sil (red), selected with puromycin, and then treated for 18 hours with taxol;

FIGS. 4a-b are analyses of HeLa cells transfected with pSuper vectors along with a co-transfection marker vector encoding the puromycin resistance gene. FIG. 4a is a series of FACS histograms depicting the cell cycle profile of transfected cells selected with puromycin and then treated with taxol (tax), thymidine (thy) or mock treated (nt) for 18 h. Cell cycle profiles of cells transfected with pSUPER are depicted in blue, while pSUPER-Sil transfected cells are in red. FIG. 4b is a Western blot analysis of vector transfected cells (pSUP) compared to cells transfected with pSUPER-Sil. Untreated samples (nt) were compared to taxol treated samples (tx). Blots were stained for Sil, cCbl, as a loading control and Cyclin A (Cyc A) as a cell cycle marker;

FIG. 5a is a bar-graph of results of an RQ PCR analysis showing SIL RNA expression levels [as determined using the RQ SIL F (SEQ ID NO:16) and R (SEQ ID NO:17) primers] in different colon carcinoma clones transfected with a tetracycline-inducible SIL siRNA expression construct, with (#+) and without (#−) the addition of tetracycline. The variability in SIL level of expression after the addition of tetracycline, is shown in blue;

FIG. 5b is a Western immunoblotting analysis showing SIL protein levels in different clones before (−) and after (+) the addition of tetracycline for 24 hours. An antibody against CBL was used as a control for loading. Note that while in clone LS#2 following tetracycline addition the level of SIL protein is markedly downregulated, in clones LS#4 and LS#6 the level of SIL protein is unchanged;

FIGS. 6a-b demonstrate that RNAi mediated knockdown of SIL results in a lower number of living cells. FIG. 6a—Photographs of cell cultures stably transfected with tetracycline-inducible SIL siRNA expression construct depicting cell growth as manifested by the color of the medium (upper lanes) and in the crystal violet staining (bottom lanes), before (−) and after (+) the addition of tetracycline. The right lanes represent clone No. 2 (where SIL is downregulated 6 times following the addition of tetracycline, see FIGS. 5a-b) and the left lanes represent clone No. 6 (where there is no change in SIL level, see FIGS. 5a-b). Note the significant decrease in crystal violet staining and the lack of change in the original reddish color of the medium in clone No. 2 plates following the addition of tetracycline demonstrating the inhibition of cell growth following tetracycline induction. Similar results were seen with additional clones (data not shown). FIG. 6b—Photographs cell cultures of various cancerous cell lines following transfection with the soluble SIL RNAi oligonucleotides having a sense strand corresponding to a nucleotide sequence as set forth in SEQ ID NO:14 (SIL siRNA 1207), SEQ ID NO:15 (SIL siRNA 2163), with the combination of the two SIL RNAi (SIL RNAi 2163+1207, a mixture of the two siRNAs) or with a scrambled RNAi (having a sense strand corresponding to SEQ ID NO:23). The tested cell lines were the LS174T (colon carcinoma), H1299 (Non Small Cell Lung Cancer, carcinoma), HeLa (cervix adenocarcinoma) and PC3 (prostate adenocarcinoma). Note the significant decrease in live cells (up to the total disappearance of living cells) in cancerous cell lines treated with the SIL RNAi 1207, 2163 and the combination of both. Similar results were observed with additional cell lines: MCF-7 (breast adenocarcinoma), PANC1 (pancreas carcinoma), U-87 (glioblastoma) and Caki-2 (kidney carcinoma) (data not shown). Altogether, these results demonstrate the impact of SIL knockdown on the growth of cancerous cell lines.

Figure 7A:
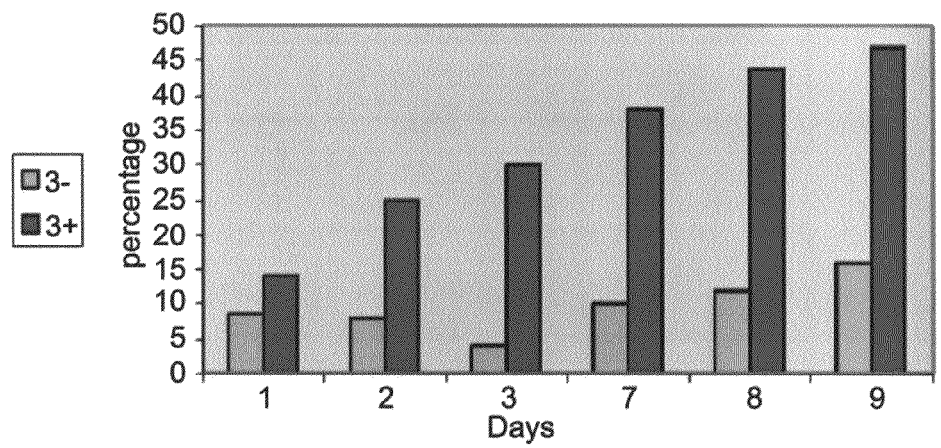
Figure 7B:
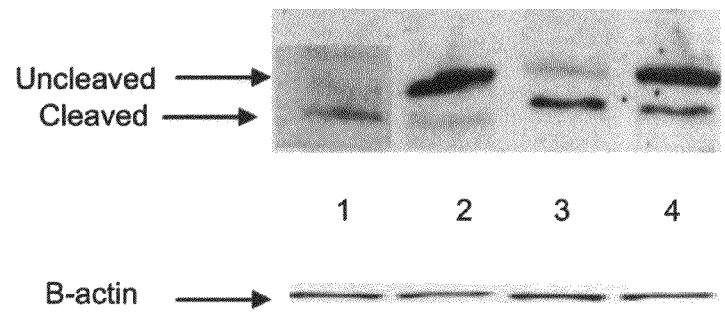

FIGS. 7a-b demonstrate that downregulation of SIL causes apoptosis. FIG. 7a—a histogram depicting flow cytometry analysis for annexin-propidium-iodide (PI) comparing the percentage of apoptosis (annexin+, PI−) before (−) and after (+) the addition of tetracycline to clone 3. This graph is a representative assay of three independent experiments. Note the significant increase in the percentage of apoptosis in cells induced by tetracycline-mediated SIL siRNA. FIG. 7b is a Western blot analysis of Caspase3 cleavage products. When apoptosis occurs, the 20 kDa band diminishes and the 17 kDa band appears as evidence of Caspase 3 cleavage. Lane 1—Positive control (apoptotic Baf3 cells-murine pro-B cells, IL-3 dependent cells, grown w/o IL-3) (MatsuweH, 2005), lane 2—Negative control—living cells, lane 3—Synchronized cells exposed to Tetracycline and Taxol for 24 hours, lane 4—Synchronized cells exposed to Taxol without Tetracycline. The loading control was Beta-actin. Note that while in synchronized cells exposed to Tetracycline and Taxol (lane 3) the level of the uncleaved band of 20 kDa Caspase-3 decreases and the level of the cleaved band of 17 kDa Caspase-3 increases, in cells exposed to Taxol without Tetracycline (i.e., no induction of SIL siRNA, lane 4) the level of the uncleaved band of 20 kDa Caspase-3 remains as in the negative control cells.

Figures 8A, 8B, 8C:
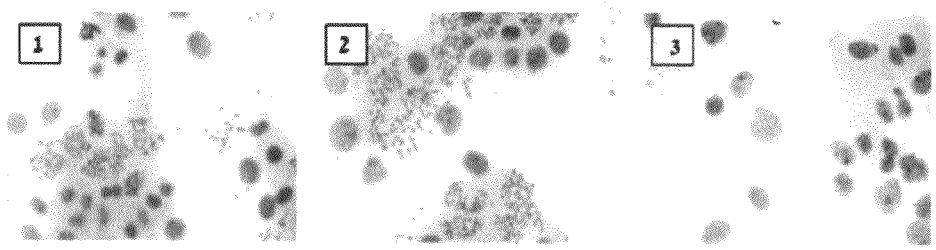
Figure 9:
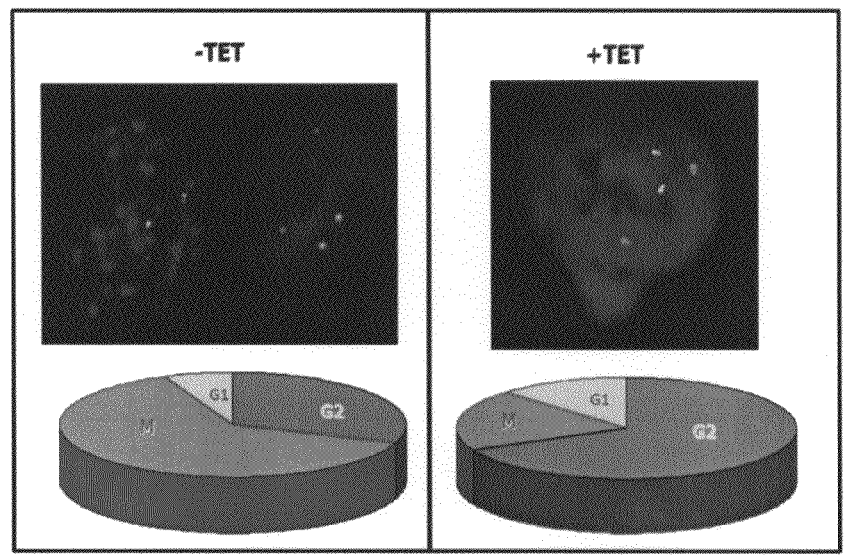
Figure 10:
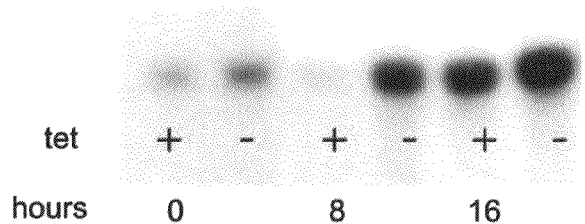

FIGS. 8a-c are photomicrographs depicting Giemza staining for cell morphology showing lower number of mitoses after exposure to colchicine in cells where SIL is downregulated. Cells with and without tetracycline were exposed to colchicine for 19 hours. The small specks are the chromosomes after treatment with hypotonic buffer and represent metaphases. FIG. 8a depicts a normal clone exposed to colchicine without tetracycline. FIG. 8b depicts clone 6 in which there is almost no change in SIL level, exposed to tetracycline and colchicine. FIG. 8c depicts clone 2 in which SIL is downregulated after exposure to tetracycline and colchicine. Original magnification, x40;

FIG. 8d depicts a flow cytometry analysis of cells stained for PI and MPM2 with or without Tetracycline; upper panels show DNA content and lower panels the dot plots obtained by co-staining with anti-MPM2 and PI. The difference in the percentage of mitotic cells is statistically significant ($p<0.05$);

FIG. 9 depicts FISH analysis of tetracycline treated (+TET) and untreated (−TET) cells after 16 hours exposure to colchicine using red and green fluorescent probes for Abl (9q34), and BCR (22), respectively. Original magnification, ×100. The pie-charts below the fluorescence photomicrographs indicate the cell-cycle distribution of 200 cells;

FIG. 10 depicts an in-situ gel phosphorylation assay depicting that CDK1 (CDC2)/Cyclin B activity is reduced in SIL knockdown cells (tet+) treated with taxol.

Figures 11A, 11B:
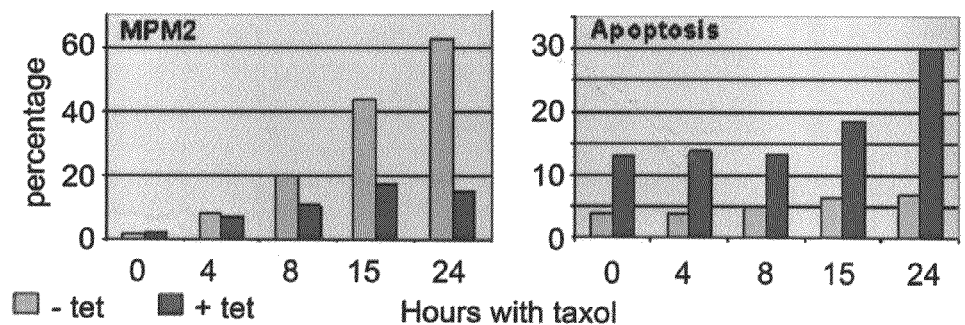

FIGS. 11a-b are histograms depicting diminished mitosis (FIG. 11a) coupled with apoptosis (FIG. 11b) of SIL knockdown cells (red, +tet). Shown is one representative experiment out of 10 similar ones;

FIGS. 12a-b depict inhibition of colon cancer tumor growth in-vivo in response to inhibition of SIL expression. Twenty female mice were injected with two-million LS2 cells. At 5 days post-injection, half of the mice were administered tetracycline in their drinking water. Every 3 days, the water was exchanged to avoid tetracycline degradation. Twice a week tumor size was measured in mice as a function of 3 axial diameters according to the formula: (X*Y*Z)/2. FIG. 12a is a data plot depicting the average growth in each group in 3 different experiments. Student's t-test was calculated for each group on each measurement day. FIG. 12b is a photograph depicting examples of tumors excised from mice which either received Tet or did not;

FIGS. 13a-c depicts in vivo escape of SIL siRNA. FIG. 13a is a histogram depicting real time quantitative PCR results showing RNA levels of SIL in tumors excised 20 and 28 days after injection (from mice participating in the experiment depicted in FIGS. 12a-b); Note that while at day 20 post-injection the level of SIL RNA was significantly reduced in tetracycline-treated mice, at day 28 post-injection there was no significant change in the level of SIL RNA between mice treated with tetracycline or untreated mice. FIGS. 13b-c are immunostaining analyses for SIL in tumors excised from tetracycline treated (FIG. 13c) or untreated (FIG. 13b) mice at day 28 after injection, demonstrating SIL expression in tumors that escaped the growth arrest. Note the similar expression pattern of SIL protein in the mice, demonstrating that the mice escaped the tetracycline-induced silencing of SIL siRNA. These figures demonstrate that the expression of SIL is absolutely essential for tumor growth.

Figure 14A:
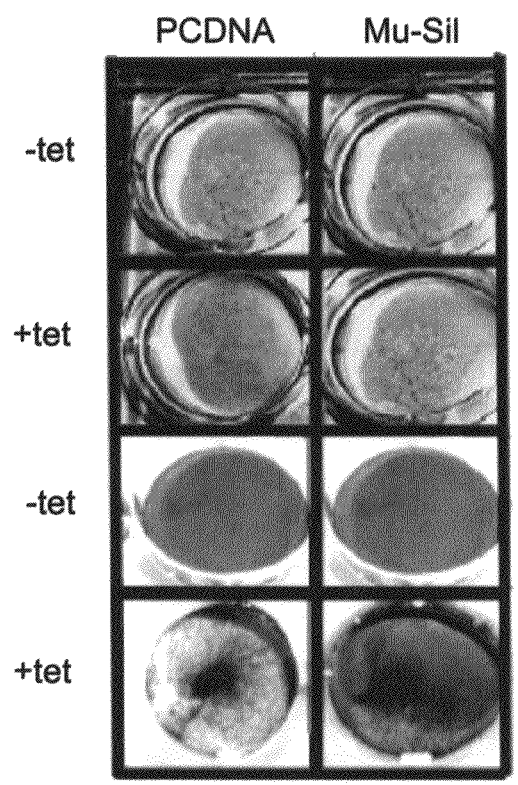
Figure 14B:
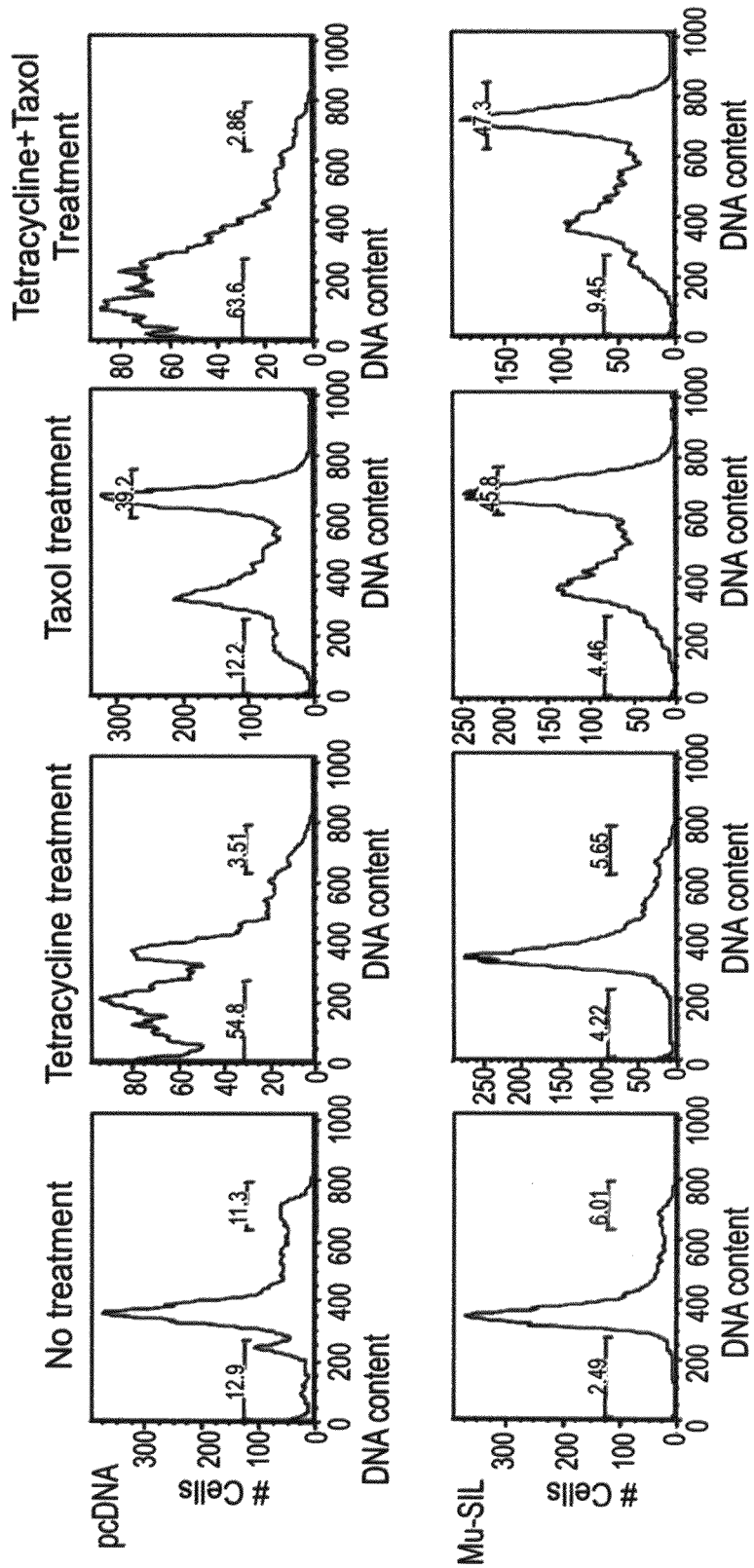
Figures 14C, 14D:
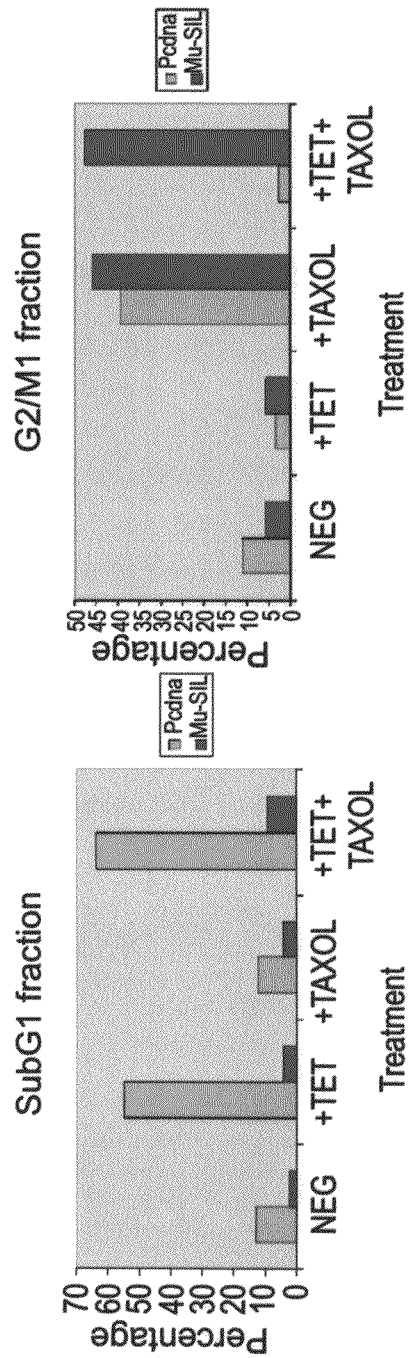

FIGS. 14a-c depict that transfection of a construct encoding murine SIL rescues the phenotype of human SIL knockdown. FIG. 14a is a series of photographs depicting the color of the medium and crystal violet staining of clone No. 2 cells post stable transfection with the PCDNA clone (left) or murine SIL (Mu-sil) (right) growing with or without tetracycline (tet). Note that while cells of clone No. 2 which were stably transfected with the PCDNA vector failed to grow, cells of the same clone which were transfected with murine SIL overcome the growth inhibition induced by SIL siRNA. FIG. 14b—a series of cell cycle analyses by flow cytometry of cells stained with PI. Clone No. 2 cells were stably transfected with either Murine Sil or an empty vector (PCDNAIII). All cells were synchronized with Thymidine and exposed to Taxol either with or without the addition of Teracycline. FIGS. 14c-d—Histograms depicting the fraction of cells in subG1 (FIG. 14c) or in G2/M (FIG. 14d) as calculated from the cell cycle analyses depicted in FIG. 14b. Altogether, these results demonstrate that ectopic expression of mouse SIL rescues the G2 phenotype and apoptosis induced by SIL knockdown; These results prove that the growth suppression and apoptosis phenotype caused by the siRNA were specifically caused by inhibition of the expression of the human SIL and definitely rule out "off target" effects.

Figure 15:
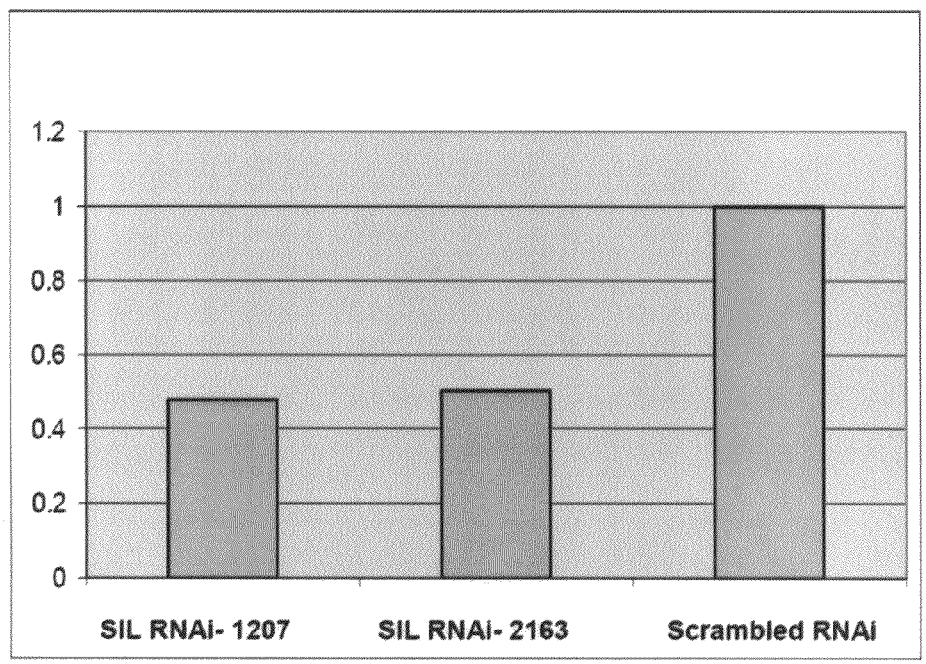

FIG. 15 is a histogram of RT-PCR analysis depicting the effect of SIL RNAi oligonucleotides on endogenous SIL. 293T cells were transfected with two oligonucleotides (1207 and 2163) which were chosen by using the BLOCK-iT™ RNAi designer (INVITROGEN) or the scrambled RNAi (used as control). Three days post transfection, RNA was extracted from the cells and used for RT-PCR. The reference gene used was β-actin. Note the significant decrease in SIL RNA level in cells transfected with the SIL RNAi oligos as compared to cells transfected with the scrambled RNAi.

Figure 16:
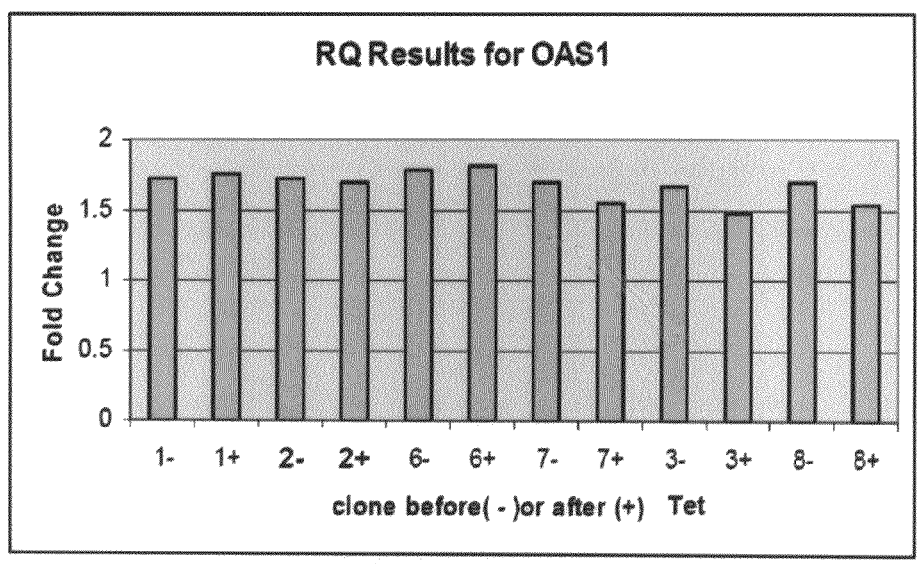

FIG. 16 is a histogram depicting RT-PCR results for OAS1 [performed using the RQ OAS1 F (SEQ ID NO:18) and RQ OAS1 R (SEQ ID NO:19) primers] following induction with Tetracycline. The X axis represents the different clones before (−) and after (+) addition of Tetracycline, while the Y axis shows the fold change in OAS1 RNA level. Note that no significant difference is observed in OAS1 level following the induction of Tetracycline. This proves that the siRNA against SIL does not induce the interferon pathway FIGS. 17a-c depict that SIL downregulation growth arrest phenotype is not caused by differentiation. FIGS. 17a-b—LS 174T cells grown with (FIG. 17b) or without (FIG. 17a) Tetracycline and stained with PAS for mucus. FIG. 17c is a histogram depicting the RT-PCR results [performed using the RQ GAL-4 F (SEQ ID NO:20) and RQ GAL-4 R (SEQ ID NO:21) primers] for the induction of GAL4 before (−) and after (+) the addition of Tetracycline in the indicated clones.

Figure 18:
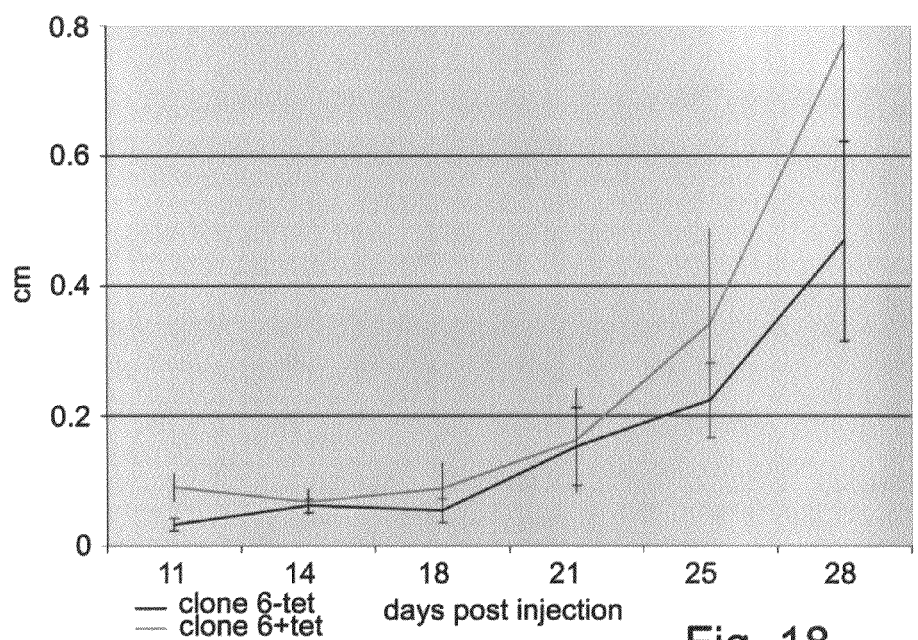

FIG. 18 is a graph depicting that tumor growth with normal SIL is not influenced by Tetracycline. Twenty female mice were injected with $2\times10^6$ of LS cells of clone No. 6, in which SIL is not downregulated following the addition of Tetracycline. Five days post injection, half of the mice received Tetracycline in their drinking water. Every three days, the water was changed to avoid Tetracycline degradation. Twice a week, tumor size was measured in all mice in 3 diameters (X*Y*Z/2). The graph shows the average growth in each group in 3 different experiments. A t-test was used to analyze each group on each measurement day. There was no statistical significant difference between the tumor growth in mice receiving Tetracycline, in fact, those tumors grew even better.

Figure 19A:
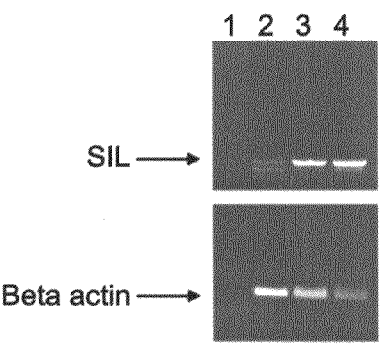
Figure 19B:
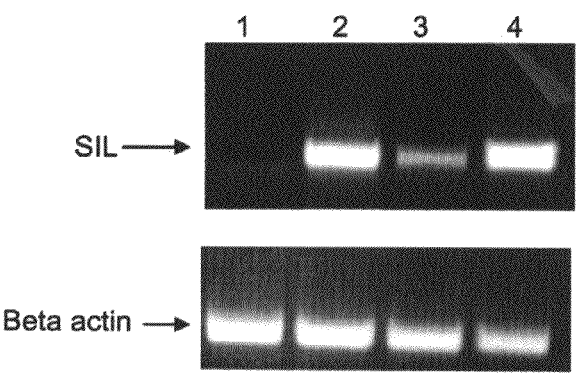
Figure 19C:
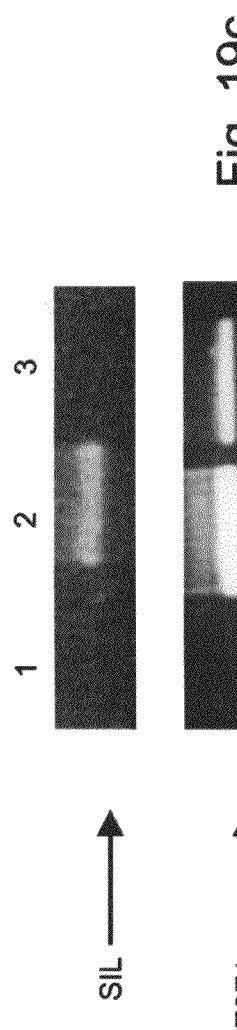
Figure 19D:
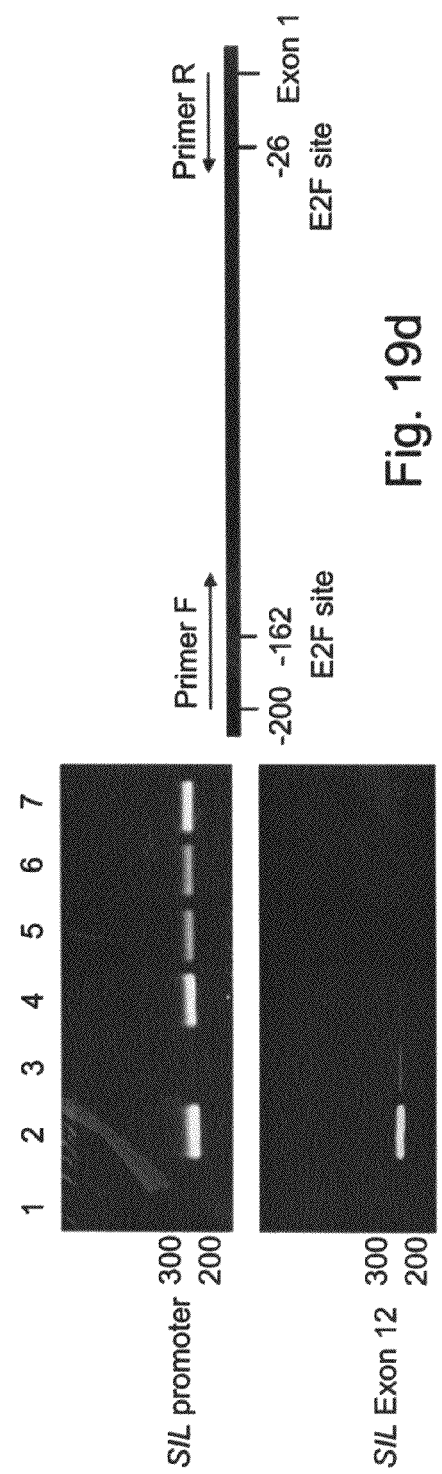

FIGS. 19a-d depict the regulation of SIL by E2F1. FIG. 19a are RT-PCR analyses of SIL RNA in WII38 cells. RT-PCR reactions were performed using the Hu-SIL F (SEQ ID NO:6) and Hu-SIL R (SEQ ID NO:7) primers. WI138, embryonic lung fibroblasts, expressing the E2F1-ER fusion protein were serum starved for 24 hours and then stimulated by 300 nM 4-OHT for the indicated time periods (t, time in hours post addition of 4-OHT): lane 1—no-DNA, lane 2—WI138 t-0, lane 3—WI138 t-4 hours, lane 4—WI138 t-8 hours. The PCR was 35 cycles. β-actin was used as control for loading. These results demonstrate that SIL RNA levels rise post induction with ectopic E2F1. FIG. 19b are RT-PCR analyses depicting SIL RNA levels post activation by endogenous E2F by E1A (using the primers set forth by SEQ ID NOs:6 and 7). Lane 1—WI38 under serum starvation, lane 2—WI-38 under serum starvation transfected with EIA, lane 3—WI-38 in growth conditions, lane 4—WI-38 in growth conditions transfected with EIA. β-actin was used as control for loading. These results demonstrate that SIL RNA levels rise post activation of the endogenous E2F by E1A; FIG. 19c—RT-PCR analyses depicting the level of SIL (using the primers set forth by SEQ ID NOs:6 and 7), E2F1 (using the primers set forth by SEQ ID NOs:12 and 13) and β-actin following transfection with shRNA for E2F1 (siRNA having a sense strand corresponding to SEQ ID NO:22, which corresponds to nucleotides 861-879 of human E2F1 as set forth by GenBank Accession No. NM_005225). Lane 1—No DNA, lane 2—Scrambled shRNA, lane 3—shRNA for E2F1. The loading control is β-actin. Note that shRNA for E2F1 downregulates SIL expression. FIG. 19d—RT-PCR analyses depicting the expression of SIL promoter (using the primers set forth by SEQ ID NOs:8 and 9) and exon 12 (using the primers set forth by SEQ ID NOs: 10 and 11) following chromatin immuno precipitation. Lane 1—No DNA, lane 2—Input before immuno-precipitation (IP), lane 3—IP with anti-HA, lane 4—IP with anti-E2F1, lane 5—IP with anti-E2F2, lane 6—IP with anti-E2F3, lane 7—IP with anti-E2F4. A schematic drawing is added to show the position of the E2F sites and of the primers used for PCR of SIL promoter. These results demonstrate that E2F1 binds SIL promoter in vivo.

DESCRIPTION OF THE PREFERRED EMBODIMENTS

The present invention is of methods of regulating proliferation of a cell population which proliferates abnormally in a subject to thereby treat in the subject a disease associated with such a cell population; and of novel pharmaceutical compositions for practicing such methods. Specifically, the present invention can be used to treat any of various types of tumors/cancers, such as those of colorectal, uterine cervical, mammary, pancreatic, pulmonary, or neurological origin.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

There is an urgent need for methods of treating diseases associated with abnormal cell proliferation, such as tumors/cancers.

Thus, the prior art fails to provide a method of harnessing SIL activity/level modulation so as to enable effective treatment of a disease associated with abnormal cell proliferation, such as a tumor/malignancy.

While reducing the present invention to practice the present inventors, as described and illustrated in Examples 1-3 and 5 of the Examples section below, surprisingly discovered that inhibition of expression of the cell cycle regulator SIL, via transfection of a SIL siRNA expression vector or soluble siRNA agents, could be used to inhibit in-vitro the growth of highly diverse types of tumor cells, such as uterine cervical, colon, mammary, pancreatic, lung carcinoma, glioblastoma, and colon carcinoma cell. Additionally, while reducing the present invention to practice, as described and illustrated in Example 4 of the Examples section which follows, the present inventors further discovered that such inhibition of SIL expression, via an inducible SIL siRNA expression vector, can be used to effectively treat tumors, such as colon cancer tumors, in a mammal. Thus, by virtue of enabling growth inhibition of highly diverse tumor cell types and by virtue of enabling inducible/tumor cell-specific treatment of in-vivo human tumor growth in a mammal, the present invention provides a novel and effective means of treating essentially any type of tumor in a human. Since it enables inducible/tumor cell-specific growth inhibition, the present invention is efficient and avoids the harmful side-effects to non-tumor cells and tissues associated with standard prior art tumor treatments involving systemic administration of cell-cycle inhibitory chemotherapeutic agents.

Thus, the present invention provides a method of regulating proliferation of a cell population which proliferates abnormally. The method is effected by contacting the cell population with at least one modulator capable of modulating in the cell population a level and/or activity of a polypeptide having an amino acid sequence at least 60 percent similar to SEQ ID NO: 5, as determined using the Standard protein-protein BLAST [blastp] software of the NCBI.

The method can be used for treating any of various diseases which are associated with an abnormally proliferating cell population, and in particular to treat a disease which is associated with an abnormally hyperproliferating cell population, such as tumors/cancers in general, and in particular cancers of the colon, uterine cervix, breast, pancreas, liver, lung, brain, retinoblastoma, skin (e.g., melanoma) or epidermal [e.g., squammous-cell carcinoma (SCC), basal cell carcinoma (BCC) and a non-melanoma skin cancer (NMSC)], lymphoma (e.g., Burkitt's lymphoma, non-Hodgkin's lymphoma) as well as various leukemias such as acute lymphoblastic leukemia (ALL), acute myeloid leukemias (AML) and chronic myeloid leukemia (CML). Other diseases with hyperproliferating cell population which can be treated by the method of the present invention include inflammatory proliferative disorders such as autoimmune proliferative disorders [e.g., rheumatoid arthritis (proliferative synovitis) and viral (e.g., EBV)-induced lymphoid proliferation], psoriasis, proliferative retinitis and ulcerative colitis and the like. As used herein, the term "treating" includes curing, alleviating, or stabilizing the disease, or inhibiting future onset or development of the disease.

As used herein, the term "disease" refers to any disease, disorder, condition or to any pathological or undesired condition, state, or syndrome, or to any physical, morphological or physiological abnormality.

Thus, the present invention provides a method of treating a disease associated with a cell population which proliferates abnormally in a subject. The method is effected by administering the at least one modulator to the subject.

The subject is preferably a homeotherm, more preferably a mammal, and most preferably a human.

A polypeptide having the amino acid sequence of SEQ ID NO: 5 (hereinafter "target polypeptide") corresponds to human SIL (GenBank Accession No. AAK51418).

According to the teachings of the present invention, the target polypeptide may have any one of various sequences, while essentially retaining the cell cycle regulatory functionality of human SIL (GenBank Accession No. AAK51418).

Preferably, the target polypeptide has an amino acid sequence whose percent similarity to SEQ ID NO: 5, as determined using the Standard protein-protein BLAST [blastp] software of the NCBI, where gap open penalty equals 11, gap extension penalty equals 1 and matrix is blosum 62, is; 60 percent, more preferably 65 percent, more preferably 70 percent, more preferably 75 percent, more preferably 80 percent, more preferably 85 percent, more preferably 90 percent, more preferably 91 percent, more preferably 92 percent, more preferably 93 percent, more preferably 94 percent, more preferably 95 percent, more preferably 96 percent, more preferably 97 percent, more preferably 98 percent, more preferably 99 percent and most preferably 100 percent.

More preferably, the target polypeptide has an amino acid sequence whose percent identity to SEQ ID NO: 5, as determined using the Standard protein-protein BLAST [blastp] software of the NCBI, where gap open penalty equals 11, gap extension penalty equals 1 and matrix is blosum 62, is; 60 percent, more preferably 65 percent, more preferably 70 percent, more preferably 75 percent, more preferably 80 percent, more preferably 85 percent, more preferably 90 percent, more preferably 91 percent, more preferably 92 percent, more preferably 93 percent, more preferably 94 percent, more preferably 95 percent, more preferably 96 percent, more preferably 97 percent, more preferably 98 percent, more preferably 99 percent and most preferably 100 percent.

Thus, the target polypeptide most preferably corresponds to SEQ ID NO: 5, which, as described above, corresponds to human SIL (GenBank Accession No. AAK51418).

Preferably, in order to decrease or abrogate proliferation of abnormally hyperproliferating cells, the level and/or activity of the target polypeptide is eliminated or decreased.

As used herein, the term "hyperproliferating cell population" refers to any cell population which proliferates at pathologically high levels in a subject, or whose decreased proliferation is desirable for any medical, cosmetic or other reason.

Alternately, in order to stimulate or increase proliferation of a hypoproliferating cell population, the level and/or activity of the target polypeptide is stimulated or increased in the hypoproliferating cell population (e.g., using the polypeptide set forth by SEQ ID NO:5 or using a polynucleotide encoding same).

As used herein, the term "hypoproliferating cell population" refers to any cell population in a subject which proliferates at pathologically low levels, or whose increased proliferation is desirable for any medical, cosmetic or other reason.

Any one of various types of modulators can be used to abrogate or decrease the level and/or activity of the target polypeptide.

Preferably, the modulator (e.g., downregulating agent) is an isolated polynucleotide (e.g., recombinantly expressed or chemically synthesized) such as an siRNA capable of inducing degradation of an mRNA encoding the target polypeptide.

Any of various siRNAs can be employed to decrease/abrogate expression/levels of the target polypeptide.

Preferably, the siRNA has a sense strand which corresponds to a nucleotide sequence which comprises SEQ ID NO: 1, 2, 14 or 15, more preferably which corresponds to SEQ ID NO: 1, more preferably which corresponds to SEQ ID NO: 2, more preferably, which corresponds to SEQ ID NO:14, more preferably, which corresponds to SEQ ID NO:15. As is described and illustrated in Example 4 of the Examples section which follows, administration of an siRNA having a sense strand corresponding to SEQ ID NO: 2 can be used to treat human colon cancer tumors in a mammal. Similarly, as is described in Examples 2-4 of the Examples section below, administration of an siRNA having a sense strand corresponding to SEQ ID NO: 2 can be used to achieve inhibition of proliferation of cancer cells of essentially any lineage, as achieved in the case of cancer cells of colorectal, pancreatic, mammary, or glial lineage.

As is further described in Example 1 of the Examples section which follows, administration of an siRNA having a sense strand corresponding to SEQ ID NO: 1 can be used to achieve inhibition of proliferation of cancer cells of uterine cervical lineage.

Moreover, as is further described in Examples 2, 3, 4 and 5 of the Examples section which follows, administration of an siRNA having a sense strand corresponding to SEQ ID NOs. 2, 14 and/or 15 can be used to inhibit cancerous cells growth by both inhibition entry into mitosis and inducement of apoptosis (cell death) of a variety of cancerous cells such as colon cancer, lung cancer, cervical cancer, prostate cancer, breast cancer, pancreatic cancer and glioblastoma.

A small interfering RNA (siRNA) molecule decreases/abrogates expression of the target polypeptide via RNA interference. RNA interference is a two step process. the first step, which is termed as the initiation step, input dsRNA is digested into 21-23 nucleotide (nt) small interfering RNAs (siRNA), by the action of Dicer, a member of the RNase III family of dsRNA-specific ribonucleases, which processes (cleaves) dsRNA (introduced directly or via a transgene or a virus) in an ATP-dependent manner. Successive cleavage events degrade the RNA to 19-21 by duplexes (siRNA), each with 2-nucleotide 3' overhangs [Hutvagner and Zamore Curr Opin Genetics and Development 12:225-232 (2002); and Bernstein, Nature 409:363-366 (2001)].

In the effector step, the siRNA duplexes bind to a nuclease complex to form the RNA-induced silencing complex (RISC). An ATP-dependent unwinding of the siRNA duplex is required for activation of the RISC. The active RISC then targets the homologous transcript by base pairing interactions and cleaves the mRNA into 12 nucleotide fragments from the 3' terminus of the siRNA [Hutvagner and Zamore Curr Op Gen Develop. 12:225-232 (2002); Hammond et al. Nat Rev Gen. 2:110-119 (2001); and Sharp. Genes Dev. 15:485-90 (2001)]. Although the mechanism of cleavage is still to be elucidated, research indicates that each RISC contains a single siRNA and an RNase [Hutvagner and Zamore, Curr Opin Gen. Develop. 12:225-232 (2002)].

Because of the remarkable potency of RNAi, an amplification step within the RNAi pathway has been suggested. Amplification could occur by copying of the input dsRNAs which would generate more siRNAs, or by replication of the siRNAs formed. Alternatively or additionally, amplification could be effected by multiple turnover events of the RISC

[Hammond et al., Nat Rev Gen. 2:110-119 (2001), Sharp Genes Dev. 15:485-90 (2001); Hutvagner and Zamore Curr Opin Gen. Develop. 12:225-232 (2002)]. Ample guidance for using RNAi to practice the present invention is provided in the literature of the art [refer, for example, to: Tuschl, ChemBiochem. 2:239-245 (2001); Cullen, Nat Immunol. 3:597-599 (2002); and Brantl, Biochem Biophys Acta 1575:15-25 (2002)].

Guidance for delivering nanoparticles containing siRNAs to cells, such as cancer cells, which express targetable specific surface markers for nanoparticle delivery so as to inhibit translation of target mRNAs in such cells is provided in the literature of the art (Schiffelers R M. et al., 2004. Cancer siRNA therapy by tumor selective delivery with ligand-targeted sterically stabilized nanoparticle. Nucleic Acids Res. 32:e149).

Synthesis of siRNA molecules suitable for use with the present invention can be effected as follows. First, the target polypeptide's mRNA sequence is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs), being enriched in regulatory protein binding sites. UTR-binding proteins and/or translation initiation complexes may interfere with binding of the siRNA endonuclease complex [Tuschl, Chem Biochem. 2:239-245]. It will be appreciated though, that siRNAs directed at untranslated regions may also be effective, as demonstrated for GAPDH wherein siRNA directed at the 5' UTR mediated about 90 percent decrease in cellular GAPDH mRNA and completely abolished protein level (http://www.ambion.com/techlib/tn/91/912.html). Second, potential target sites are compared to an appropriate genomic database (e.g., human, mouse, rat etc.) using any sequence alignment software, such as the BLAST software available from the NCBI server (www.ncbi.nlm.nih.gov/BLAST/). Putative target sites which exhibit significant homology to other coding sequences are filtered out. Qualifying target sequences are selected as template for siRNA synthesis. Preferred sequences are those including low G/C content as these have proven to be more effective in mediating gene silencing as compared to those with G/C content higher than 55 percent. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

The selected siRNAs can be chemically synthesized oligonucleotides (using e.g., solid phase synthesis) or can be encoded from plasmids in order to induce RNAi in cells following transfection (using e.g., the pRETRO-SUPER vector). Recently, retrovirus- or lentivirus-delivered RNAi were developed and were found efficient in long-term gene silencing in vivo [Hao D L., et al., 2005, Acta. Biochim. Biophys. Sin. (Shanghai), 37(11): 779-83].

As is described and illustrated in Example 4 of the Examples section which follows, administration of an siRNA of the present invention can be used to treat human colon cancer tumors in a mammal. As is described in Example 5 of the Examples section which follows, administration of an siRNA of the present invention can be used to treat breast cancer (e.g., breast adenocarcinoma), pancreas carcinoma, glioblastoma, kidney carcinoma, lung cancer (e.g., Non Small Cell Lung Carcinoma), cervical cancer (e.g., cervix adenocarcinoma), and prostate cancer (e.g., prostate adenocarcinoma). As is further described in Examples 1-2 of the Examples section below, administration of an siRNA of the present invention can be used to achieve inhibition of proliferation of cancer cells of widely varying lineages, namely of colorectal, uterine cervical, pancreatic, mammary, pulmonary or glial lineage, and as such can be used for inhibiting proliferation of essentially any type of cancer.

Another modulator which can be used to decrease/eliminate the level/activity of the target polypeptide is a DNAzyme. A DNAzyme is a molecule capable of specifically cleaving an mRNA transcript or DNA sequence of the target polypeptide. DNAzymes are single-stranded polynucleotides which are capable of cleaving both single and double stranded target sequences (Breaker, R. R. and Joyce, G. Chemistry and Biology, 1995, 2:655; Santoro, S. W. and Joyce, G. F. Proc. Natl. Acad. Sci. U.S.A., 1997, 943:4262). A general model (the "10-23" model) for the DNAzyme has been proposed. Namely, "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions [Santoro, S. W. and Joyce, G. F. Proc. Natl. Acad. Sci. U.S.A., 1997, 943:4262; for review of DNAzymes, refer, for example, to Khachigian, L M., Curr Opin Mol Ther. 4:119-21 (2002)].

Examples of construction and amplification of synthetic, engineered DNAzymes recognizing single and double-stranded target cleavage sites have been disclosed in U.S. Pat. No. 6,326,174 to Joyce et al., in which DNAzymes of similar design directed against the human urokinase receptor were recently observed to inhibit urokinase receptor expression, and successfully inhibit colon cancer cell metastasis in vivo (Itoh et al, 20002, Abstract 409, Ann Meeting Am Soc Gen Ther., http://www.asgt.org). In another application, DNAzymes complementary to bcr-abl oncogenes were successful in inhibiting the oncogenes expression in leukemia cells, and lessening relapse rates in autologous bone marrow transplant in cases of CML and ALL.

A further modulator which can be used to decrease/eliminate the level/activity of the target polypeptide is an antisense polynucleotide (e.g., antisense oligonucleotide).

Design of suitable antisense molecules must be effected while considering two aspects important to the antisense approach. The first aspect is delivery of the oligonucleotide into the cytoplasm of the abnormally proliferating cells, while the second aspect is design of an oligonucleotide which specifically binds the designated mRNA within cells in a way which inhibits translation thereof.

The term "oligonucleotide" refers to a single stranded or double stranded oligomer or polymer of ribonucleic acid (RNA) or deoxyribonucleic acid (DNA) or mimetics thereof. This term includes oligonucleotides composed of naturally-occurring bases, sugars and covalent internucleoside linkages (e.g., backbone) as well as oligonucleotides having non-naturally-occurring portions which function similarly to respective naturally-occurring portions.

Oligonucleotides designed according to the teachings of the present invention can be generated according to any oligonucleotide synthesis method known in the art such as enzymatic synthesis or solid phase synthesis. Equipment and reagents for executing solid-phase synthesis are commercially available from, for example, Applied Biosystems. Any other means for such synthesis may also be employed; the actual synthesis of the oligonucleotides is well within the capabilities of one skilled in the art and can be accomplished via established methodologies as detailed in, for example, "Molecular Cloning: A laboratory Manual". Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988) and "Oligonucleotide Synthesis" Gait, M. J., ed. (1984) utilizing solid phase chemistry, e.g. cyanoethyl phosphoramidite followed by deprotection, desalting and purification by for example, an automated trityl-on method or HPLC.

The oligonucleotide of the present invention is of at least 17, at least 18, at least 19, at least 20, at least 22, at least 25, at least 30 or at least 40, bases specifically hybridizable with SIL RNA sequence (e.g., the nucleic acid sequence set forth by GenBank Accession No. NM_003035)

The oligonucleotides of the present invention may comprise heterocylic nucleosides consisting of purines and the pyrimidines bases, bonded in a 3' to 5' phosphodiester linkage.

Preferably used oligonucleotides are those modified in either backbone, internucleoside linkages or bases.

The prior art teaches of a number of delivery strategies which can be used to efficiently deliver oligonucleotides into a wide variety of cell types [see, for example: Luft, J Mol Med. 76:75-6 (1998); Kronenwett et al., Blood 91:852-62 (1998); Rajur et al., Bioconjug Chem. 8:935-40 (1997); Lavigne et al., Biochem Biophys Res Commun. 237:566-71 (1997) and Aoki et al., (1997) Biochem Biophys Res Commun. 231:540-5 (1997)].

In addition, algorithms for identifying those sequences with the highest predicted binding affinity for their target mRNA based on a thermodynamic cycle that accounts for the energetics of structural alterations in both the target mRNA and the oligonucleotide are also available [see, for example, Walton et al, Biotechnol Bioeng 65:1-9 (1999)]. Such algorithms have been successfully used to implement an antisense approach in cells. For example, the algorithm developed by Walton et al., enabled scientists to successfully design antisense oligonucleotides for rabbit beta-globin and mouse tumor necrosis factor-alpha transcripts. The same research group has also reported that the antisense activity of rationally selected oligonucleotides against three model target mRNAs in cell culture as evaluated by a kinetic PCR technique proved effective in almost all cases, including tests against three different targets in two cell types with phosphodiester and phosphorothioate oligonucleotide chemistries.

Furthermore, several approaches for designing and predicting efficiency of specific oligonucleotides using an in vitro system were also published (Matveeva et al., Nature Biotechnology 16:1374-1375 (1998)].

Several clinical trials have demonstrated safety, feasibility and activity of antisense oligonucleotides. For example, antisense oligonucleotides suitable for the treatment of cancer have been successfully used [Holmlund et al., Curr Opin Mol Ther. 1:372-85 (1999)]. Treatment of hematological malignancies via antisense oligonucleotides targeting c-myb gene and p53 has been shown in clinical trials to be tolerated by patients [Gerwitz Curr Opin Mol Ther. 1:297-306 (1999)]. Antisense-mediated suppression of human heparanase gene expression has been reported to inhibit pleural dissemination of human cancer cells in a mouse model [Uno et al., Cancer Res 61:7855-60 (2001)]. The use of Bcl-2 antisense oligonucleotide (oblimersen) for cancer chemotherapy is currently in phase III clinical trials (Koziner B., 2004. Oncology (Williston Park). 18:32-8; Coppelli F M, Grandis J R., 2005. Curr Pharm Des. 11:2825-40).

Thus, the current consensus is that recent developments in the field of antisense technology which, as described above, have led to the generation of highly accurate antisense design algorithms and a wide variety of oligonucleotide delivery systems, enable an ordinarily skilled artisan to design and implement antisense approaches suitable for downregulating expression of known sequences without having to resort to undue trial and error experimentation.

An additional modulator which can be used to decrease/eliminate the level/activity of the target polypeptide is an enzyme, such as a ribozyme, which can specifically cleave the target polypeptide. A ribozyme molecule capable of specifically cleaving an mRNA transcript encoding the target polypeptide can be used to decrease/abrogate expression/levels of the target polypeptide. Ribozymes are useful for the sequence-specific inhibition of gene expression by the cleavage of mRNAs encoding proteins of interest [Welch et al., Curr Opin Biotechnol. 9:486-96 (1998)]. The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers and specific somatic mutations in genetic disorders [Welch et al., Clin Diagn Virol. 10:163-71 (1998)]. The effectiveness of ribozymes has also been demonstrated in studies involving transgenic animals, gene target validation and/or pathway elucidation. Several ribozymes are in various stages of clinical trials. ANGIOZYME was the first chemically synthesized ribozyme to be studied in human clinical trials. ANGIOZYME specifically inhibits formation of vascular endothelial growth factor receptor, a key component in the angiogenesis pathway. HEPTAZYME, a ribozyme designed to selectively destroy hepatitis C virus RNA, was found effective in decreasing hepatitis C viral RNA in cell culture assays (Ribozyme Pharmaceuticals, Incorporated). Ribozymes have been approved for use in several clinical trials involving ribozyme gene therapy for HIV/AIDS patients.

Yet an additional modulator which can be used to decrease/eliminate the activity of the target polypeptide is an inhibitor molecule (ligand) which can specifically bind the target polypeptide, and/or a molecule involved in mediating regulation of cellular proliferation by the target polypeptide, in such a way as to decrease/eliminate the level/activity of the target polypeptide. Means of obtaining and therapeutically utilizing specific ligands of target molecules which are capable of decreasing or eliminating the activity of the latter are well known in the art and are routinely practiced by the ordinarily skilled artisan. The ligand may comprise, for example, a portion of the target polypeptide and/or a portion of a biomolecule which is involved in a functional molecular interaction between the target polypeptide and the biomolecule. It will be appreciated that such a ligand will be capable of substantially blocking/interfering with the functional molecular interaction to thereby decrease/eliminate the activity of the target polypeptide.

Depending on the application and purpose, a modulator of the present invention can be administered to the subject in any of various ways so as to decrease/eliminate activity/level of the target polypeptide in the abnormally proliferating cell population, to thereby treat the disease in the subject.

One of ordinary skill in the art, such as a physician or veterinarian, as appropriate, in particular an artisan specialized in the disease to be treated, will possess the necessary expertise for adapting the teachings of the present invention for suitably treating a particular disease of the present invention in a given subject. One of ordinary skill in the art will possess the necessary expertise for selecting a suitable administration route for suitably administering a modulator of the present invention, for selecting a suitable regimen for administering the modulator, and for suitably monitoring the disease during treatment so as to achieve a desired therapeutic outcome in the subject.

Administering a modulator such as an siRNA may be advantageously effected by administering the siRNA to the subject so as to achieve delivery of the modulator to the abnormally proliferating cell population.

As is described in the Examples section below, administration of an siRNA modulator of the present invention can be used to achieve inhibition of proliferation and inducement of apoptosis of cancer cells of essentially any lineage, as achieved using cancer cells of uterine cervical, colorectal, pancreatic, mammary, pulmonary or glial lineage.

Administering a modulator which is polypeptide-based or nucleic acid-based to the cell population may alternatively be advantageously effected by delivering to the cell population a polynucleotide which comprises or encodes the modulator. Alternately, such administration may be effected by administering to the cell population a nucleic acid construct which comprises the polynucleotide, and a transcription control sequence operatively linked to the polynucleotide enabling expression of the polynucleotide in the cell population. The transcription control sequence may advantageously be inducible so as to render controllable the expression of the modulator by the nucleic acid construct.

As is described in Example 1 of the Examples section below, expression in cervical cancer cells of a nucleic acid construct encoding a modulator of the present invention, such as an siRNA having a sense strand corresponding to SEQ ID NO: 1 can be used to inhibit the growth of such cells.

As is described in Example 2 of the Examples section which follows, expression in colon, breast, pancreatic lung or glioblastoma tumor cells of a nucleic acid construct encoding a modulator of the present invention, such as an siRNA having a sense strand corresponding to SEQ ID NO: 2, under the regulatory control of a tetracycline-inducible promoter can be used to inhibit the growth of such cells.

As is further described in Example 4 of the Examples section below, expression in colon tumor cells of a nucleic acid construct encoding a modulator of the present invention, such as an siRNA having a sense strand corresponding to SEQ ID NO: 2, under the regulatory control of a tetracycline-inducible promoter can be used to cure a mammal bearing such tumors.

Thus, the present invention provides a recombinant polynucleotide which comprises a nucleic acid sequence where the nucleic acid sequence encodes and/or comprises a modulator of the present invention.

Thus, the present invention further provides a nucleic acid construct which comprises a recombinant polynucleotide of the present invention and at least one expression control sequence which is operatively linked to the recombinant polynucleotide, and which is capable of controlling expression of the recombinant polynucleotide in a host cell.

Effective delivery of a nucleic acid construct/viral vector capable of expressing a desired therapeutic agent at a selected pathological site has been demonstrated by numerous studies. Of particular interest is an approach which utilizes computer-aided tomography (CAT) to direct needle injection into a tumor. Such a technique has been demonstrated in the treatment of non-small cell lung cancer by Kauczor et al. [(1999) Eur. Radiol. 9:292-296]. In a prospective clinical phase I trial, six patients with non-small cell lung cancer and a mutation of the tumor suppressor gene p53 were treated by CAT-guided intratumoral gene therapy. Ten milliliters of a vector solution (replication-defective adenovirus expressing wild-type p53 cDNA) were injected under CAT guidance. The CAT-guided gene therapy was easily performed in all six patients without intervention-related complications. Besides flu-like symptoms, no significant adverse effects of gene therapy were noted. After 28 days, four of the six patients showed stable disease at the treated tumor site, whereas other tumor manifestations progressed. This study demonstrated that tomography-guided injection is suitable for performing intratumoral gene therapy.

The nucleic acid construct can be administered to the subject according to any one of various gene therapy approaches so as to achieve expression of genetic sequences encoding the modulator in the abnormally proliferating cell population.

Successful implementation of gene therapy has been demonstrated by numerous published prior art studies. By May 2001, 532 gene therapy protocols have been approved for evaluation in clinical trials [Stephan et al. (2002) Oncologist 7(1):46-59]. Numerous ongoing studies involve gene therapy for treating various forms of human cancer, as follows.

Sterman et al. (Hum. Gene Ther. 9:1083-92) conducted a phase I trial of adenovirus mediated intrapleural Herpes-simplex virus (HSV)-thymidine kinase (tk)/ganciclovir (GCV) gene therapy in patients with mesothelioma. A replication-incompetent adenoviral vector containing the HSV-tk gene under control of the Rous sarcoma virus promoter-enhancer was introduced into the pleural cavity of patients with malignant mesothelioma followed by 2 weeks of systemic therapy with GCV at a dose of 5 mg/kg twice daily. Side-effects were minimal and included fever, anemia, transient liver enzyme elevations, and bullous skin eruptions as well as a temporary systemic inflammatory response in those receiving the highest dose.

This study demonstrated that intrapleural administration of an adenoviral vector containing the HSV-tk gene leads to detectable gene transfer when delivered at high doses as well as being tolerated by treated individuals.

Klatzmann et al. [Hum. Gene Ther. 9:2595-2604] used an HSV-tk/GCV system in which allogeneic M11 cells were transduced by retrovirus in vitro and injected into the surgical cavity (sc) after debulking of glioblastoma. Despite extensive surgery for glioblastoma, residual tumor cells always lead to relapse. After a 7-day transduction period, GCV was administered for 14 days. Twelve patients with recurrent glioblastoma were treated without serious adverse side effects. Twenty-five percent of the patients survived longer than 12 months. Four months following treatment, 4 of the 12 patients treated had no recurrence. One patient was still free of detectable recurrence, steroid free and independent, 32 months following treatment. Thus, injections of M11 retroviral vector cells producing tk resulted in significant therapeutic responses as well as being well tolerated by the treated individuals.

Stewart et al. [(1999) Gene Ther. 6:350-363] conducted a phase I study in which an E1- and E3-deleted adenovirus encoding IL-2 (Ad-CA-IL-2) was directly injected into sc deposits of melanoma and breast cancer. Local inflammation was observed at the site of injection in 60 percent of the patients, however, no severe side-effects were reported. Incomplete local tumor regression occurred at the site of injection in 24 percent of the patients. No Ad5E1 sequences were detected either prior to, or following injection, indicating the absence of replication-competent virus. Anti-adenovirus and neutralizing antibody titers were elevated 1 month following injection in all patients.

This trial, confirmed the safety of use of adenoviral vectors for gene delivery in humans and demonstrates successful transgene expression even in the face of preexisting immunity to adenovirus.

Palmer et al. [Hum. Gene Ther. 10:1261-8] used a recombinant retrovirus to transduce expression of IL-2 in melanoma cells. These IL-2-secreting tumor cells were then used to vaccinate individuals. Twelve patients were vaccinated sc 1, 2, or 3 times with approximately 107 irradiated, autologous, IL-2-secreting tumor cells. Treatment was well tolerated, with local reactions at 11 of 24 injection sites and minor systemic symptoms of fever and headache following 6 injections. One patient developed antitumor delayed-type hypersensitivity after the first vaccination and showed an increased response after the second vaccination. This study illustrated that vaccination with autologous, genetically engineered tumor cells is both feasible and safe and effective at inducing antitumor delayed-type hypersensitivity and anti-tumor cytotoxic T-lymphocytes.

Herman et al. [(1999) Hum. Gene Ther. 10:1239-1249] also studied direct in situ gene therapy for adenocarcinoma of the prostate using a replication-deficient adenovirus expressing tk and administration of GCV. Patients received injections of increasing concentrations of virus into the prostate under ultrasound guidance. GCV was then given intravenously (iv) for 14 days (5 mg/kg every 12 hours). Eighteen patients received 100 million to 100 billion IU. All cultures of blood and urine specimens were negative for growth of adenovirus. One patient at the highest dose level developed spontaneously reversible thrombocytopenia and hepatotoxicity. Three patients achieved an objective response, documented by a fall in serum PSA levels by 50 percent or more, that was sustained for 6 weeks to 12 months.

Clearly gene therapy can be applied safely and effectively to human tumors by injection into pleural or tumor cavities or by direct tumor injection. The dosage of virus indicated in these trials caused at most mild side-effects.

Oncolytic virotherapy using adenovirus d11520 (Onyx-015)—d11520 (Pfizer Corp. Groton, Conn., USA), an E1B—55 kD gene deleted adenovirus was the first genetically engineered agent to be thoroughly tested in humans. The agent is an adenovirus modified to replicate in, and selectively kill, cells that harbor p53 mutations. Over 250 cancer patients have so far been treated in approximately 10 clinical trials (Phases I-III). These studies showed that this modified virus is well tolerated by patients following intratumoral, intraperitoneal, hepatic arterial and intravenous administration. Viral replication was tumor selective and was documented following administration by all routes. Although single agent efficacy was limited, co-administration with chemotherapy exhibited anti-tumoral activity. These clinical research results demonstrated the potential of this novel treatment platform [Kirn (2001) Expert Opin. Biol. Ther. 1:525-38]. It will be appreciated that Onyx Pharmaceuticals was granted U.S. Pat. No. 5,677,178 covering methods for the treatment of p53 related cancers in 1997. The patent specifically covers the use of modified adenoviruses and other DNA viruses which lack viral proteins that bind to p53, for the treatment of cancer patients whose tumors lack p53 function. Other patents include U.S. Pat. No. 5,846,945 and EP Pat. No. 09491077.8 [Cohen (2001) Curr. Opin. Investig. Drugs 2:1770-5].

Shalev et al. [(2000) J. Urol. 163:1747-50] reviewed a case in which 52 patients were repeatedly injected with an adenovirus-expressing tk. Although toxicity increased from 35 percent up to 75 percent, in patients who received from 2-4 cycles of therapy, all toxic events were mild and resolved completely. No additional toxicity was noted. Results obtained from 28 patients indicated a mean decrease of 44 percent in PSA in 43 percent of the patients, showing that direct injection of HSV-tk, followed by iv GCV, was safe and effective, even in multiple trials.

Other examples of active or completed clinical trials are listed hereinbelow:

(i) Gene therapy of malignant gliomas: a Phase I study of IL-4-HSV-TK gene-modified autologous tumor to elicit an immune response. 1998 Active Principal Investigators: M. Bozik, H. Okada, M. Lotze; Collaborator: J. Barranger.

(ii) Gene therapy of melanoma, Phase I, University of Michigan, Ann Arbor, Mich. 1992 Completed; Principal Investigator: G. Nabel; Collaborator: L. Huang.

(iii) Gene therapy of gynecological cancers, Phase I, Singapore General Hospital, Singapore 1996 Completed; Principal Investigator: K. Hui; Collaborator: L. Huang.

(iv) Gene therapy for c-erB-2 overexpressing ovarian and breast cancers, Phase I. 1996 Active; Principal Investigators: D. Hortobagyi, M.-C. Hung; Collaborator: L. Huang.

(v) A Phase II, multicenter open label study to evaluate effectiveness and safety of two treatment regimens of Ad5CMV-p53 administered by intra-tumoral injections in 78 patients with recurrent squamous cell carcinoma of the head and neck. 1997 Active; Principal Investigator: S. Agarwala; Collaborator: J. Barranger.

(vi) A Phase I study in patients with recurrent or metastatic squamous cell carcinoma of the head and neck using SCH 58500 (rAd/p53) administered by single intratumoral injection. 1996 Active; Principal Investigator: S. Agarwala; Collaborator: J. Barranger.

(vii) IL-12 gene therapy of melanoma using direct injection of tumors with genetically engineered autologous fibroblasts (Phase II study) 1996 Active Principal Investigator: H. Tahara; Collaborator: J. Barranger.

(viii) IL-12 gene therapy for head and neck cancer melanoma using direct injection of tumors with genetically engineered autologous fibroblasts (Phase II study) 1996 Active; Principal Investigator: H. Tahara; Collaborator: J. Barranger.

(ix) IL-12 gene therapy using direct injection of tumors with genetically engineered autologous fibroblasts. 1996 Active; Principal Investigators: H. Tahara, M. Lotze; Collaborator: J. Barranger.

(x) Phase 1 study of percutaneous injections of wild-type adeno-virus p53 construct (Adeno-p53) for hepatocellular carcinoma. 1997 Active; Principal Investigators: C. Belani, C. Can; Collaborator: J. Barranger.

Clinical trial of gene therapy for Gaucher disease. 1996 Active; Principal Investigator: J. Barranger.

(xi) Gene therapy for Canavan's disease, Phase I/II, University of Aukland, New Zealand. 1994 Active; Principal Investigators: M. During, P. Leone (Liposomes were produced in HGTAL by L. Huang)

(xii) Gene therapy for cystic fibrosis, Phase I, National Lung and Blood Institute, London, UK; 1995 Completed; Principal Investigators: E. Alton, D. Geddes, B. Williamson (xiii) Gene therapy for cystic fibrosis, Phase I, University of Oxford, Oxford, UK 1996 Completed; Principal Investigators: S. Hyde, D. Gill, C. Higgins (xiv) Gene therapy for cystic fibrosis by multiple dosing, Phase I, University of Oxford, Oxford, UK 1997 Completed; Principal Investigators: D. Gill, S. Hyde, C. Higgins (Liposomes were produced in HGTAL by L. Huang).

In 1999 a clinical trial was conducted at the university of Pennsylvania in order to investigate gene transfer of the ornithine transcarbamylase (OTC) gene. An adenoviral vector containing the OTC gene was injected into adults suffering from a disease associated with OTC partial deficiency. After receiving the highest dose tested, an 18 year old man developed systemic inflammatory response and died a few days following treatment.

Following this tragedy, gene therapy trials raised many concerns in the press, the public, the scientific and medical communities and government agencies, although, in fact, there was no scientific reason to believe that the problems of concern are specific to gene therapy. In fact, results from the numerous trials conducted to date indicate that while the gene therapy approach has its limitations, these limitations are the exception rather than the rule [Sigel (2002) The Journal of Infectious Diseases 185:S52-S57] and that in some cases this approach is even safer and more effective than commonly practiced treatment approaches.

In the United States, gene therapy trials are conducted under guidelines similar to those practiced for other highly innovative biotechnological approaches. An FDA site-inspection random sampling of 15 percent of active gene therapy clinical research applications, uncovered several sites at which areas for improvement were found and a few requiring regulatory or administrative action. However, the incidence of problems found was no greater than that seen in FDA inspections of efficacy trials described in applications for pharmaceutical agents.

An NIH report assessing the safety and toxicity of adenovirus (Ad)-based gene transfer concluded that "human gene transfer experiments using Ad-based vectors should continue-with caution" [Human Gene Therapy(2002) 13:3-13].

A modulator, polynucleotide or nucleic acid construct of the present invention can be administered to a subject of the present invention per se, or it can be formulated as a pharmaceutical or a cosmetic composition where it is mixed with suitable carriers or excipients.

Thus, the present invention provides a pharmaceutical composition for treatment of a disease of the present invention, and which comprises a pharmaceutically acceptable carrier, and, as an active ingredient, a modulator, recombinant polynucleotide and/or nucleic acid construct of the present invention.

Guidance regarding obtaining and using a pharmaceutical composition of the present invention is provided hereinbelow.

The present invention can be used to treat any one of various diseases which are associated with an abnormally proliferating cell population.

Preferably, the disease is associated with excessive proliferation of a cell population (i.e. a hyperproliferating cell population).

Examples of diseases associated with excessive proliferation of a cell population include metastatic tumors, malignant tumors, benign tumors, cancers, pre-cancers, hyperplasias, warts, polyps, growths, inflammatory proliferative disorders such as autoimmune proliferative disorders [e.g., rheumatoid arthritis (proliferative synovitis) and viral (e.g., EBV)-induced lymphoid proliferation], psoriasis, proliferative retinitis, ulcerative colitis and the like.

Preferably, the method is used to treat a tumor, more preferably a malignant tumor, more preferably a malignant tumor of gastrointestinal origin, more preferably a tumor of colon origin. Most preferably, the method is used to treat colon cancer.

Preferably, the method is used to treat a gastrointestinal disease, a uterine disease, a glandular disease, a pulmonary disease, or a neurological disease.

Preferably, the gastrointestinal disease is a colorectal disease, most preferably colon cancer.

Preferably, the method is used to treat a malignant tumor such as lung cancer, cervical cancer, prostate cancer and breast cancer, pancreatic cancer and glioblastoma.

As is described and illustrated in Example 4 of the Examples section which follows, administration of a modulator of the present invention can be used to treat human colon cancer tumors in a mammal.

As is described and illustrated in Example 1 of the Examples section which follows, administration of a modulator of the present invention can be used to inhibit growth of cervical cancer cells. Thus, the present invention can be advantageously used to treat a uterine disease associated with abnormal cell proliferation.

Preferably, the uterine disease is a uterine cervical disease, most preferably cervical cancer.

As is described and illustrated in Example 2 of the Examples section which follows, administration of a modulator of the present invention can be used to inhibit growth of glandular, lung or neurological cancer cells. Thus, the present invention can be advantageously used to treat a glandular, pulmonary or neurological disease associated with abnormal cell proliferation.

Preferably, the glandular disease is a mammary disease or a pancreatic disease.

Preferably, the mammary disease is breast cancer, more preferably mammary adenocarcinoma.

Preferably, the pancreatic disease is pancreatic cancer, more preferably pancreatic epithelioid carcinoma.

Preferably, the pulmonary disease is lung cancer, more preferably non-small cell lung carcinoma.

Preferably, the neurological disease is a glial disease, most preferably glioblastoma/glioma.

It will be appreciated that the present invention is particularly useful for treating diseases whose pathology is associated with abnormally proliferating cells in which SIL is expressed at high levels (refer, for example, to: Aplan, Lombardi et al. 1991; Izraeli, Colaizzo-Anas et al. 1997; Erez, Perelman et al. 2004). These are numerous and varied, and include, for example, acute lymphoblastic leukemia (ALL), acute myeloid leukemias (AML), chronic myeloid leukemia (CML), Burkitt's lymphoma, non-Hodgkin's lymphoma, small-cell lung cancer, prostate cancer, melanoma, liver cancer, and teratocarcinoma.

Alternately, the present invention can be used to treat diseases whose pathology is associated with abnormally proliferating cells in which SIL is expressed at low levels, such as glioma. This is a particularly surprising teaching of the present invention since the prior art teaches that glioma cells express SIL at low levels, in sharp contrast to various other types of cancer cells.

Examples of cancers which can be treated using the method of the present invention include adrenocortical carcinoma, bladder cancer, ductal breast cancer, invasive intraductal breast cancer, breast-ovarian cancer, colorectal adenoma, hereditary nonpolyposis colorectal cancer, colorectal cancer type 1, 2, 3, 6 or 7, dermatofibrosarcoma protuberans, endometrial carcinoma, esophageal cancer, gastric cancer, fibrosarcoma, glioblastoma multiforme, multiple glomus tumors, hepatoblastoma, hepatocellular cancer, acute non-lymphocytic leukemia, Li-Fraumeni syndrome, liposarcoma, lynch cancer family syndrome II, male germ cell tumor, mast cell leukemia, medullary thyroid carcinoma, medulloblastoma, meningioma, multiple endocrine neoplasia, myxosarcoma, neuroblastoma, osteosarcoma, ovarian cancer, serous ovarian cancer, ovarian carcinoma, -ovarian sex cord tumors, pancreatic endocrine tumors, familial nonchromaffin paraganglioma, pilomatricoma, pituitary tumor, renal cell carcinoma, retinoblastoma, rhabdoid tumors, rhabdomyosarcoma, soft tissue sarcoma, head and neck squamous cell carcinoma, T-cell acute lymphoblastic leukemia, Wilms' tumor type 1 or 2, etc.

Classes of precancers amenable to treatment via the method of the present invention include acquired small or microscopic precancers, acquired large lesions with nuclear atypia, precursor lesions occurring with inherited hyperplastic syndromes that progress to cancer, and acquired diffuse hyperplasias and diffuse metaplasias. Examples of small or microscopic precancers include HGSIL (high grade squamous intraepithelial lesion of uterine cervix), AIN (anal intraepithelial neoplasia), dysplasia of vocal cord, aberrant crypts (of colon), PIN (prostatic intraepithelial neoplasia). Examples of acquired large lesions with nuclear atypia include tubular adenoma, AILD (angioimmunoblastic lymphadenopathy with dysproteinemia), atypical meningioma, gastric polyp, large plaque parapsoriasis, myelodysplasia, papillary transitional cell carcinoma in-situ, refractory anemia with excess blasts, and Schneiderian papilloma. Examples of precursor lesions occurring with inherited hyperplastic syndromes that progress to cancer include atypical mole syndrome, C cell adenomatosis and MEA. Examples of acquired diffuse hyperplasias and diffuse metaplasias include AIDS, atypical lymphoid hyperplasia, Paget's disease of bone, post-transplant lymphoproliferative disease and ulcerative colitis.

As used herein a "pharmaceutical composition" refers to a preparation of one or more of the modulators (active ingredients) described herein with other chemical components such as physiologically suitable carriers and excipients. The purpose of a pharmaceutical composition is to facilitate administration of active ingredients to the subject.

Herein the term "active ingredients" refers to modulators of the present invention accountable for the therapeutic effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered active ingredients. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols. The pharmaceutical composition may advantageously take the form of a foam or a gel.

Techniques for formulation and administration of drugs may be found in "Remington's Pharmaceutical Sciences," Mack Publishing Co., Easton, Pa., latest edition, which is incorporated herein by reference.

Suitable routes of administration include any of various suitable systemic and/or local routes of administration.

Suitable routes of administration may, for example, include the inhalation, oral, buccal, rectal, transmucosal, topical, transdermal, intradermal, transnasal, intestinal and/or parenteral routes; the intramuscular, subcutaneous and/or intramedullary injection routes; the intrathecal, direct intraventricular, intravenous, intraperitoneal, intranasal, and/or intraocular injection routes; and/or the route of direct injection into a tissue region of a subject of the present invention.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active ingredients with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active ingredient doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration via the inhalation route, the active ingredients for use according to the present invention are conveniently delivered in the form of an aerosol/spray presentation from a pressurized pack or a nebulizer with the use of a suitable propellant, e.g., a fluorochlorohydrocarbon such as dichlorodifluoromethane, trichlorofluoromethane, dichloro-tetrafluoroethane; carbon dioxide; or a volatile hydrocarbon such as butane, propane, isobutane, or mixtures thereof. In the case of a pressurized aerosol, the dosage unit may be determined by providing a valve to deliver a metered amount. Capsules and cartridges of, e.g., gelatin for use in a dispenser may be formulated containing a powder mix of the active ingredients and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredients may be in powder form for constitution with a suitable vehicle, e.g., sterile, pyrogen-free water based solution, before use.

The pharmaceutical composition of the present invention may also be formulated for ocular administration (e.g., eye drops, for the treatment of proliferative retinitis). Methods of preparing pharmaceutical compositions suitable for ocular administration are described in U.S. Pat Appl. Publ. Nos. 20060134226 and 20040009181. For example, the active ingredient can be stirred in saline and buffer (e.g., 1.5% by weight of composition in 10% by volume saline and buffer).

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (modulators of the present invention) effective to prevent, alleviate or ameliorate symptoms of a disease of the present invention, or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide plasma or brain levels of the active ingredients which are sufficient to achieve a desired therapeutic effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of the composition to be administered will be dependent on the subject being treated, the severity of the affliction, the manner of administration, the judgment of the prescribing physician, etc.

As mentioned, the active ingredients may be also formulated for topical application (e.g., as a cosmetic composition) along with a dermatologically acceptable carrier.

The phrase "dermatologically acceptable carrier", refers to a carrier which is suitable for topical application onto the skin, i.e., keratinous tissue, has good aesthetic properties, is compatible with the active agents of the present invention and any other components, and is safe and non-toxic for use in mammals. An effective amount of carrier is selected from a range of about 50% to about 99.99%, preferably from about 80% to about 99.9%, more preferably from about 90% to about 98%, and most preferably from about 90% to about 95%, by weight, of the composition.

In order to enhance the percutaneous absorption of the active ingredients (e.g., the siRNA of the present invention), one or more of a number of agents can be added to the pharmaceutical or cosmetic compositions including, but not limited to, dimethylsulfoxide, dimethylacetamide, dimethylformamide, surfactants, azone, alcohol, acetone, propylene glycol and polyethylene glycol.

The carrier utilized in the compositions of the invention can be in a wide variety of forms. These include emulsion carriers, including, but not limited to, oil-in-water, water-in-oil, water-in-oil-in-water, and oil-in-water-in-silicone emulsions, a cream, an ointment, an aqueous solution, a lotion or an aerosol. As will be understood by the skilled artisan, a given component will distribute primarily into either the water or oil/silicone phase, depending on the water solubility/dispersibility of the component in the composition.

It will be appreciated that such a pharmaceutical or cosmetic composition can be used to treat any abnormal cell proliferation, such as psoriasis.

Compositions of the present invention may, if desired, be presented in a pack or dispenser device, such as an FDA approved kit, which may contain one or more unit dosage forms containing the active ingredients. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

Thus, the present invention provides an article of manufacture which comprises packaging material and a pharmaceutical composition of the present invention identified in print in or on the packaging material for treatment of a disease of the present invention, where the pharmaceutical composition comprises a pharmaceutically acceptable carrier, and a therapeutically effective amount of a modulator, recombinant polynucleotide and/or nucleic acid construct of the present invention.

Thus, the present invention clearly and convincingly provides a novel and effective method. pharmaceutical and cosmetic compositions for treating, via modulation of levels/activity of SIL and SIL-like proteins, a disease whose pathology is associated with abnormally proliferating cells, such as cancer, retinoblastoma, autoimmune proliferative disorders [e.g., rheumatoid arthritis (proliferative synovitis) and viral (e.g., EBV)-induced lymphoid proliferation], psoriasis, proliferative retinitis and ulcerative colitis.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

General Materials and Experimental Methods

Cell Culture, Transfections and Retroviral Infections
Culture:
LS174T and H1299 cells were grown with 10% fetal bovine serum, 2 mM glutamine, 100 mcg/ml streptomycin and 100 units/ml Penicillin in RPMI (Gibco BRL Paisley, Scotland). PC3, MCF-7, PANC1, U-87, Caki-2 and HeLa cells were grown 10% fetal bovine serum, 2 mM glutamine, 100 mcg/ml streptomycin and 100 units/ml Penicillin in DMEM (Gibco BRL Paisley, Scotland). Cells were maintained at 37° C. in a humidified incubator with 5% $CO_2$.

Retroviral Infections:
293T cells were co-transfected with a mixture of three plasmids: pSUPER Retro-E2F1 (encoding RNAi targeting E2F1, (30), pCGP (encoding the gag-pol of Maloney murine leukemia virus) and pMDG (encoding VSVG env protein). 48 hours post transfection, the medium was filtered through 0.45 micron and 8 mcg/ml polybrene was added. The viral supernatant was added to a T-Cell leukemic cell-line, plated a day before on a 6 well plate at a concentration of $2 \times 10^5$. The cells were centrifuged 45 minutes, 1800 RPM at room temperature. The procedure was repeated 24 hours later. On the following day colonies were selected with Puromycin 10 mcg/ml.

Transfections:
different cancer cell lines were transfected using the siIM-PORTER™ liposomal transfection reagent (UPSTATE, cat. #64-101), JetPEI™ (Polyplus-transfection, Illkirch, France) or Lipofectamine 2000 (Invitrogen) according to the manufacturers protocols.

E2F Induction:
WI38 human embryonic lung fibroblasts stably expressing the Estrogen Receptor were induced for E2F1 with 4-hydroxytamoxifen (OHT) (300 nM) as published (30).

Chromatin Immunoprecipitation—
was performed as published (30).

Generation of an Inducible System for SIL Downregulation:
pTer-plasmid carrying the Tetracycline (Tet) operator carrying an shRNA specific for the human SIL was transfected into LS 174T colon cancer cells carrying the Tetracycline (Tet) repressor (22). Plasmids: pTR, pSuper and pTER were kindly provided by H Clevers H, (22). For primers and oligonucleotide sequences see Table 1. SIL-shRNA: Construction of pSuper/pTER was performed as published (31). Two other duplexes of dsRNA oligonucleotides were designed using the BLOCK-iT™ RNAi designer, by INVITROGEN (Table 1, hereinbelow). Murine Sil: murine Sil cDNA sequence was inserted BamHI-Ecorl into pcDNA3 and also to pQCXIP, a retroviral expression vector (CLONTECH).

TABLE 1

Sequences of oligonucleotides used in the present study (Additional sequences are detailed in text)

| Name | SEQ ID NO: | Sequence |
|---|---|---|
| Hu-SIL F | 6 | 5'-GACTACTTCAGGCACAGATTC-3' |
| Hu-SIL R | 7 | 5'-ATGCATGCCAACACACTG-3' |
| SIL promoter F | 8 | 5'-CCGCAGTTCTCCAAGAAGAC-3' |
| SIL promoter R | 9 | 5'-GAACTGAGGCGGCAAAC-3' |
| SIL Exon 12 F | 10 | 5'-GAGACACTGCAAAGTAAGACAG-3' |
| SIL Exon 12 R | 11 | 5'-GTGGAGGGTCTTATAGGATACTC-3' |
| SIL shRNA F | 3 | 5'-GATCCCCaagacaactgctgttgaag acTTCAAGAGAgtatcaacagcagttgta tTTTTTGGAAA-3' |
| SIL shRNA R | 4 | 5'-AGCTTTTCCAAAAAaagacaactgct gttgaagacTCTCTTGAAgtcttcaacag cagttgtcttGGG-3' |
| SIL stealth_1207 | 14 | 5'-GGGCUUGCUGUUUGCGAUACAUAUU-3' |
| SIL stealth_2163 | 15 | 5'-CCAUCUUACUGUUCCACAAACGUUU-3' |
| RQ SIL F | 16 | 5'-ATGCATATCGGTTCCTCACAGA-3' |
| RQ SIL R | 17 | 5'-ACTCCATTTGTCTTCCAGCTTG-3' |
| RQ OAS1 F | 18 | 5'-CTCCTGGATTCTGCTGGCTGA-3' |
| RQ OAS1 R | 19 | 5'-GGATGCTGCCTGGAGTGTG-3' |
| RQ GAL-4 F | 20 | 5'-AGGGCTCACAGCTCGAAGAAC-3' |
| RQ GAL-4 R | 21 | 5'-TTGATAGCAAAGCTCTTGCCTG-3' |
| sh E2F1 | 22 | 5'-GACGTGTCAGGACCTTCGT-3' |
| E2F1 F | 12 | 5'-CCAAGTCTGCCCAGAAAGCTC-3' |
| E2F1 R | 13 | 5'-GGAATGGTGACAACATGCTGG-3' |
| Scrambled siRNA | 23 | 5'-ACUGCGCUACCAUCGUGCC-3' |

Protein Purification and Western Blotting:
were done as published (8).

RNA Extraction:
$3\times10^5$ cells were seeded in wells of a six-well plate in the presence or absence of Doxycycline (Sigma-Aldrich, corn). After 24 hours RNA was extracted with TRIzol Reagent (GibcoBRL). Purified RNA (0.5 µg) was retrotranscribed with MLV-RT reverse transcriptase (GibcoBRL).

Real Time Quantitative (RQ) PCR:
RQ-PCR expression assays were done for SIL, OAS1 and GAL-4, using SYBR Green (Applied Biosystems, Warrington, UK). Primers (Sigma-Aldrich, USA) were designed according to Primer-Express software guidelines (Applied-Biosystems). β-Actin was used as an internal standard. The RQ-PCR reactions were performed using Applied Biosystems 7900HT prism real-time PCR instrument (Taqman; Perkin-Elmer/Applied Biosystems, Foster City, Calif.) as published (32).

Chemical Staining:
Crystal-violet staining: as published (22). Periodic acid-Schiff (PAS) staining: cells were washed with PBS, incubated in 1% periodic acid and stained with SCHIFF'S Reagent (Merck). Giemsa staining: cells were grown in 10 cm plates followed by incubation with Colcemid (Biological Industries, Beit-Haemek, Israel) for 16 hours, washed with PBS and subjected to Red Blood Cells hypotonic Lysis Buffer (NH4Cl 41.5 gm, KNCO3-5GM, EDTA 1 ml, H2O to 5 liter). Following cytospin, cells were fixated in May Grunwald, rinsed with water and stained with Giemsa (Sigma-Aldrich Company, Rehovot, Israel), for 7 minutes.

Cell Cycle Synchronization and Analysis:
Cell Cycle Synchronization:
Prometaphase synchronized cells were obtained by treating exponentially growing cells with 2.5 mM thymidine for 17 hours, washing twice with PBS buffer, growing them in fresh medium for 9 hours and then re-treating the cells with 2.5 mM thymidine for 16 hours. The double thymidine block was followed by a 4 hour release after which cells were treated with Taxol for the indicated times.

Flow Cytometry Analysis (FACS):
Cells were analyzed by a two-color flow cytometry using the FACScan (BD Biosciences). For each sample, 5,000 events were collected and analyzed using standard protocols. Antibodies used: anti Mitotic protein monoclonal (MPM2; an antibody that reacts with phosphorylated mitotic proteins and is a biochemical marker of mitosis) (Upstate Waltham, Mass., USA), FITC-conjugated goat anti-mouse IgG (BIO-SOURCE, Camarillo, Calif.) MPM-2 reactive cells were considered at mitosis (33). Annexin-Propidium Iodide (PI) analysis was done using Roche Diagnostics kit, Mannheim Germany.

Fluorescence In Situ Hybridization (FISH) Probes and Procedures: Cells were concentrated by cytospin and fixed with methanol: acetic acid (3:1). The LSI BCR/ABL and LSI BCR/ABL extra signal dual-color DNA probe kits were used (Vysis; Downers Grove, Ill.; http://www.vysis.com). FISH was performed according to the standard FISH protocol developed by Esa et al. (34).

Cdc2/Cyclin B1 Kinase Assay:
Cell lysates (80 µg of proteins) were incubated with 1 µg anti-Cyclin B1 antibody (H-433, Santa Cruz) and 30 µl of protein A conjugated agarose beads (Santa Cruz) at 4° C. for 4 hours. After washing three times with lysis buffer and once with reaction buffer, the immunoprecipitated complex was collected and incubated at 25° C. in 30 µl of kinase reaction mixture containing 50 mM Tris-HCl (pH 7.4), 10 mM $MgCl_2$, 1 mM DTT, 10 µM ATP, 5 µCi of $\gamma^{32}P$-ATP, and 0.5 mg/ml of histone H1 for 30 min. The reaction was terminated by the addition of 10 µl of 4×SDS-PAGE sample buffer and boiling for 5 minutes.

In Vivo Experiments:
All experiments involving animals were approved by the institutional animal care and use committee. Six-to eight-week-old female NOD SCID mice (Weizzman Institute, Rehovot Israel) were injected subcutanaously into the right flanks with $2\times10^6$ exponentially growing LS 174T cells in 200 mcl. of sterile PBS (pH 7.4). Tumor growth was confined to local masses and did not affect animal survival over a 3 month observation period. Tumor volume was measured in the three dimensions with a caliper. Animals with tumor burden >2000 mm³ were sacrificed. Mice were treated with 2 mg/ml Doxycycline (Sigma) in 2.5% sucrose in their drinking water or with 2.5% sucrose as control, from day 5 after cells injection. The drinking water was changed twice a week to avoid Doxycycline toxic metabolites.

Histological Analyses:

After the animals were sacrificed, tumor was removed, fixed in 4% paraformaldehyde, dehydrated, embedded in paraffin, and sectioned. Sections were stained with Hematoxylin and Eosin (HE) by standard procedures. For each section the number of mitosis per high power field was counted by a pathologist who counted in a blindly manner, i.e., the pathologist was not aware of the treatment the mice received. Immunohistochemical analyses: as published (8).

Example 1

Growth Inhibition of Cervical Cancer Cells via Inhibition of Sil Cellular Expression Methods of treating diseases associated with abnormal cell proliferation, such as tumors, for example cervical cancer, are urgently needed. A theoretically potent strategy for treating such diseases would be via modulation of levels/activity of proteins which are involved in regulating the cell cycle. While various such approaches have been attempted in the prior art, these are associated with disadvantages such as suboptimal efficacy and undesirable side-effects. While reducing the present invention to practice the present inventors, as described herein, have clearly and surprisingly demonstrated for the first time that modulation of cellular SIL expression can be used to inhibit growth of abnormally proliferating cells, such as cervical cancer cells, and hence can be used to treat tumors such as cervical cancer, thereby overcoming the limitations of the prior art.

Materials and Methods:

Plasmid Construction and In-Vitro Mutagenesis:

For achieving RNA interference (RNAi) of SIL expression in cancer cells, the pSUPER RNAi System (Brummelkamp, T. et al., 2002. Science 296:550-553; http://www.bio-protech.com.tw/databank/pSUPER_Protocol.pdf) was used to assemble a vector for expression of a SIL siRNA having a sense strand corresponding to the DNA oligonucleotide 5'-GGTTCTCTGACAGCAGACG-3' (SEQ ID NO: 1; nucleotides 624-642 of human SIL-encoding sequence GenBank Accession No. NM_003035/gi:4506958; for further description see Campaner S., et al., Mol. And Cell. Biol. 25: 6660-6672, 2005). For the silencing of a specific gene, the pSUPER vector is used in concert with a pair of custom oligonucleotides that comprise a unique 19-nt sequence derived from the mRNA transcript of the gene targeted for suppression (the "N-19 target sequence"). The N-19 target sequence corresponds to the sense strand of the pSUPER-generated siRNA, which in turn corresponds to a 19-nt sequence within the mRNA. In the mechanism of RNAi, the antisense strand of the siRNA duplex hybridizes to this region of the mRNA to mediate cleavage of the molecule.

Cell Culture and Transfection:

Cervical cancer cells (HeLa) were cultured in Dulbecco's modified Eagle's medium (DMEM) supplemented with 10 percent bovine calf serum, 100 units per milliliter penicillin, and 100 micrograms per milliliter streptomycin sulfate. HeLa cells were transfected using Lipofectamine Plus (Invitrogen) using standard protocols; for a 60-mm plate 2.5 micrograms of total vector DNA was used.

Experimental Results

Sil Knock-Down Impairs the Spindle Checkpoint Response:

To substantiate the physiological role of Sil and its involvement in the mitotic checkpoint, expression vector-mediated RNA interference assays were performed, as previously described (Brummelkamp, T. et al., 2002. Science 296:550-553). Efficient suppression of Sil expression could be achieved by cotransfecting a puromycin resistance vector and then selecting cells with that antibiotic (FIG. 1), or by using a double-transfection protocol (FIG. 2a). Silencing of Sil for 72 to 96 hours, but not for 48 hours, affected cell survival and cell cycle distribution (FIG. 2b). In further experiments HeLa cells were transfected with the Sil siRNA expression vector and, after 24 hours, were challenged with taxol or nocodazole for an additional 18 hours. The spindle checkpoint activation, measured by the mitotic index and MPM2 staining, showed a reduced metaphase arrest in cells with suppressed Sil expression (lanes S) compared to the control mock-transfected population (FIG. 3a, lanes V). Similar results were obtained when either taxol or nocodazole was used. The apoptotic index (FIG. 3a) and G2/M accumulation (FIG. 3b) of Sil-downregulated cells was comparable to control cells. Moreover, cell cycle profiles of untreated cells or thymidine-blocked cells did not show relevant differences between Sil-suppressed cells and control samples (FIG. 4a). Downmodulation of SIL protein expression was verified via Western immunoblotting assay (FIG. 4b). As observed in experiments using phosphorylation-mutant Sil proteins (data not shown), Sil-suppressed cells showed lower Cdc2/cyclin B1 activity that correlated with reduced phosphorylation of Cdc2 T-161 (FIG. 1). Thus, the SIL siRNA having a sense strand corresponding to SEQ ID NO: 1 is capable of delaying entry into mitosis (delaying cell division), however, has no statistical significant effect on apoptosis. Thus, Sil silencing regulates cell growth by affecting the spindle checkpoint response.

Conclusion:

The presently disclosed results teach for the first time that compounds capable of decreasing or preventing SIL protein expression, such as SIL siRNA, can be used to delay cell division in tumor cells, such as cervical cancer cells.

Example 2

Growth Inhibition of Breast, Colon, Pancreatic, Lung, and Glioblastoma Cancer Cells Via Inhibition of Cellular Sil Expression Methods of treating diseases associated with abnormal cell proliferation, such as tumors, for example breast, colon, pancreatic, lung, and glioblastoma cancer, are urgently needed. As mentioned above, a theoretically potent strategy for treating such diseases would be via modulation of levels/activity of proteins which are involved in regulating the cell cycle. While various such approaches have been attempted in the prior art, these are associated with disadvantages such as suboptimal efficacy and undesirable side-effects. While reducing the present invention to practice the present inventors, as described below, have clearly and surprisingly demonstrated for the first time that modulation of cellular SIL expression can be used to inhibit growth of abnormally proliferating cells, such as breast, colon, pancreatic, lung, and glioblastoma cancer cells, and hence can be used to treat tumors such as breast, colon, pancreatic, lung, and glioblastoma cancer, thereby overcoming the limitations of the prior art.

Experimental Results:

As described in Example 1, above, a SIL siRNA having a sense strand corresponding to SEQ ID NO: 1 was found to be capable of inhibiting entrance to cell mitosis. In order to determine whether different SIL siRNAs could be used to inhibit growth and further induce death (apoptosis) of tumor cells, and whether the siRNA approach could be used to inhibit proliferation of cancer cells other than cervical cancer cells, experiments were performed in which a vector for expression of the SIL siRNA having a sense strand corresponding to the DNA 5'-AAGACAACTGCTGTTGAAGAC-3' (SEQ ID NO: 2; nucleotides 2643-2663 of human SIL-encoding sequence GenBank Accession No. NM_003035/gi:4506958)]) was transfected into the following cancer cell lines: MCF-7 breast adenocarcinoma, PANC1 pancreas epithelioid carcinoma, H1299 non-small cell lung carcinoma, U-87 glioblastoma, or LS174T colon carcinoma cells (the latter obtained from Hans Clevers; van de Wetering, M. et al., 2003. EMBO Rep 4: 609-15). The toxicity of the treatment on the transfected cancer cells was then assessed.

Surprisingly, transfection of the SIL siRNA-expression vector was observed to specifically inhibit growth of each of the aforementioned and highly diverse mammary adenocarcinoma, pancreas epithelioid carcinoma, non-small cell lung carcinoma, glioblastoma, and colon carcinoma cell lines (Data not shown). The toxic effect of SIL siRNA on glioblastoma was especially unexpected since the prior art teaches that SIL expression levels in gliomas are very low, in sharp contrast to levels of SIL expression which are known to be high in numerous types of cancer cells, as described above.

Conclusion:

The presently disclosed results surprisingly teach for the first time that compounds capable of decreasing or preventing SIL protein expression, such as SIL siRNA having a sense strand corresponding to the DNA corresponding to SEQ ID NO: 2, can be used to inhibit proliferation of highly diverse types of tumor cells, such as breast adenocarcinoma, pancreas epithelioid carcinoma, non-small cell lung carcinoma, glioblastoma, and colon carcinoma. As such, it is presently disclosed for the first time that inhibition of SIL expression/activity can be utilized to treat essentially any type of tumor.

Example 3

Growth Inhibition of Colon Cancer Cells via Inhibition of Cellular Sil Expression Using Transfection with a Tetracycline-Inducible Sil siRNA Expression Vector Methods of treating diseases associated with abnormal cell proliferation, such as tumors, for example colon cancer, are urgently needed. As described above, a theoretically potent strategy for treating such diseases would be via modulation of levels/activity of proteins which are involved in regulating the cell cycle. While various such approaches have been attempted in the prior art, these are associated with disadvantages such as suboptimal efficacy and undesirable side-effects. While reducing the present invention to practice the present inventors, as described hereinbelow, have clearly and surprisingly demonstrated for the first time that inhibition of cellular SIL expression, via transfection with an inducible SIL siRNA expression vector, can be used to effectively inhibit the in-vivo growth in a mammal of abnormally hyperproliferating cells such as human gastrointestinal tumor cells, specifically human colon cancer cells, thereby overcoming the limitations of the prior art.

Materials and Methods:

Tetracycline-Inducible RNAi Expression Vector:

A pSUPER based construct for expression of a SIL siRNA having a sense strand corresponding to the DNA 5'-AAGACAACTGCTGTTGAAGAC-3' (SEQ ID NO: 2) was assembled as published in: Brummelkamp et al., 2002. Science 296:550-553. In brief, human SIL-specific oligonucleotides (100 pmol of each) were phosphorylated using T4 polynucleotide kinase in a total volume of 50 microliters for 30 minutes. To anneal the oligonucleotides, the mixture was incubated at 95 degrees centigrade for 5 minutes and was cooled slowly. Afterwards, 1 microliter of this mixture was ligated into pSuper vector that had been digested with BglII and HindIII and treated with calf intestinal phosphatase. The forward oligonucleotide used was: 5'-GATCCCCaagacaactgctgttgaagacTTCAAGAGAgtct-tcaacagcagttgtcttTTTTTGGA AA-3' (SEQ ID NO: 3); and the reverse primer used was: 5'-AGCTTTTCCAAAAAaagacaactgctgttgaagacTCTCTTGAAgtcttcaacagcagttgtcttGG G-3' (SEQ ID NO: 4). (The lower case letters refer to the final siRNA stem; the upper case letters refer to the siRNA loop).

Experimental Results:

A tetracycline inducible RNAi-mediated knockdown of SIL expression (human SIL protein: GenBank Accession No. AAK51418; SEQ ID NO: 5) was engineered in the colon cancer cell line LS 174T (obtained from Hans Clevers; van de Wetering, M. et al., 2003. EMBO Rep 4: 609-15). In this system the inhibitory RNA sequence is transcribed only after the addition of tetracycline to the medium. Several stable clones were generated with various degrees of SIL knockdown as judged by both RNA, via real time quantitative PCR (RQ-PCR, FIG. 5a) and protein levels (FIG. 5b). Since RNAi by introduction of short hairpin (sh) RNAs occasionally induces interferon-inducible genes (Bridge, A. J. et al., 2003. Nat Genet 34: 263-4), the level of the interferon inducible gene OAS1 was examined as a control. This gene has previously been reported to be induced nonspecifically by double stranded RNA. The level of OAS 1 did not change after the addition of Tetracycline (FIG. 16).

The phenotype of cell number reduction caused by SIL knockdown could result by different mechanisms: induction of differentiation, cell death or perturbation of the cell cycle. Differentiated colon cells demonstrate a rise in the expression levels of the GAL4 gene (22). To test if SIL downregulation induced expression level of the GAL4 gene, the LS 174T cells were grown with or without Tetracycline. As is shown in FIGS. 17a-c, there was no change in GAL4 expression levels after downregulation of SIL. Thus, the difference in growth could not be attributed to increased differentiation.

Exposure of the cells to tetracycline was shown to cause arrest in cell growth in correlation to the magnitude of SIL downregulation (FIG. 6a). This cessation of growth was caused by induction of apoptosis as measured by the levels of annexin positive cells (FIG. 7a) and the caspase 3 cleavage assay (FIG. 7b).

To determine if the downregulation of SIL influences the ability of cells to complete a proper mitosis, cells with and without tetracycline were exposed to colchicine for 19 hours. Morphological analysis via Giemza staining showed that the number of mitoses in cells with low levels of SIL was much lower than with SIL (FIGS. 8a-c). To observe the mitoses biochemically, the antibody MPM2, a mouse monoclonal antibody raised against phosphorylated mitotic proteins, was used (FIG. 8d). This antibody allows a clear differentiation between the G2 fraction and the M fraction of the cell cycle. This analysis confirmed that SIL knockdown cells arrested in G2 and did not enter mitosis when synchronized by mitotic checkpoint poisons such as colchicine or taxol.

To further substantiate this finding colchicine-arrested cells were hybridized to fluorescence in-situ hybridization (FISH) probes for chromosome 9 and 22. The SIL knockdown cells were not in mitosis but displayed a clear pattern of doublet chromatid hybridization characteristic of the G2 phase (FIG. 9).

Since the major regulator of mitotic entry is the CDK1 (CDC2)-Cyclin B complex, in order to see if the delay in mitotic entry of SIL knockdown cells was associated with a decreased activity of this kinase, a kinase assay for determining the activity of CDK1-CyclinB complex was performed. The CDK1 complex was immunoprecipitated at different times following taxol exposure and its activity was measured in-vitro. There was a marked delay in the activation of CDK1 in SIL knockdown cells (FIG. 10). The lack of activation of CDK1 could explain the arrest in G2.

To examine the temporal relationship between the apoptosis and the cell cycle phenotype of SIL knockdown cells, the cells were synchronized at S-G2 with double thymidine block, and then treated with taxol. At different time points after exposure to taxol cells were harvested and analyzed for mitosis by staining with the MPM2 antibody and for apoptosis by measurement of the sub-G1 fraction by staining with propidium iodide. At each time point there were fewer cells in the SIL knockdown group in mitosis. In parallel with increasing exposure time to taxol there was a marked increase in apoptosis (FIGS. 1a-b). This pattern suggests that the knockdown of SIL slows or perturbs the entrance to mitosis coupled with activation of apoptosis, thus inducing cell death of cancerous cells.

Thus, the above-described results clearly and surprisingly demonstrate for the first time that downmodulation of SIL activity/levels, in particular via transfection with an inducible SIL siRNA expression vector, can be used to regulate the growth of gastrointestinal cells characterized by abnormal growth, such as gastrointestinal cancer cells, in particular human colon cancer cells. As such, the presently disclosed results surprisingly teach for the first time that inhibition of SIL expression/activity can be used to treat gastrointestinal tumors, such as colon cancer.

Example 4

Treatment of Human Tumors In-Vivo in a Mammal Via Inhibition of Sil Expression

As mentioned above, methods of treating diseases associated with abnormal cell proliferation, such as cancer, are urgently needed, and a theoretically potent strategy for treating such diseases would be via modulation of activity/levels of proteins which are involved in regulating the cell cycle. Various such approaches have been attempted in the prior art, however these are associated with disadvantages such as sub-optimal efficacy and/or harmful side-effects. While reducing the present invention to practice, the present inventors, as described hereinbelow, have convincingly and surprisingly demonstrated for the first time that inhibition of SIL expression can be used to effectively treat a disease whose pathogenesis is associated with abnormally proliferating cells, such as a gastrointestinal cancer, specifically human colon cancer, thereby overcoming the limitations of the prior art.

Experimental Results:

To study the requirement of SIL expression for tumor growth in-vivo, 2 million LS clone #2 (LS2) colon cancer cells transfected with a tetracycline-inducible SIL siRNA expression vector (described in Example 3 above) were injected subcutaneously to establish human colon cancer cell tumors in immunodeficient NOD/SCID mice. Tetracycline was added to the drinking water 5 days after the injection. Five experiments with a total 20 female mice in each group were conducted. The growth of tumors in the tetracycline-treated group was substantially and significantly reduced (FIGS. 12a-b). Induction of RNAi-mediated knockdown of SIL by feeding mice with tetracycline resulted in a substantial suppression of tumor growth. As expected, there was no effect of treatment with Tetracycline on the growth of tumors derived from clone No. 6, in which SIL shRNA has nearly no effect on SIL levels (FIG. 18). After three weeks post-injection, the tumors in the +Tet (SIL knockdown) escaped repression and started growing at the same doubling time as those not receiving tetracycline. There could be at least two explanations for their escape, either there was silencing of the short hairpin RNA (shRNA) expression and cessation of SIL activity/level downmodulation, or that acquired mutations allowed growth of the cells despite a continuous knockdown of SIL. To distinguish between these possibilities the tumors were analyzed for Sil RNA levels. As shown in FIGS. 13a-c, SIL was in fact expressed in the growing tumors excised at day 28, suggesting that either the shRNA was not expressed or was not active in these cells. Thus, it can be concluded that the inhibited tumors in fact displayed renewed growth only after escaping the RNAi-mediated SIL downmodulation, and hence that SIL is critical for growth of the cells in the in-vivo context.

To determine whether the phenotype observed in the tetracycline-induced cells is caused by the knockdown of the human SIL and not by an off-target effect of the shRNA construct, the murine SIL which is not affected by the human SIL shRNA was transfected to into clone 2 cells. In these cells the addition of tetracycline reduces the levels of the human but not the mouse SIL. After the addition of tetracycline, the clones stable for murine SIL entered mitosis properly and survived and proliferated more than the control clone transfected with an empty vector PCDNA3 (FIGS. 14a-c). Thus, the apoptosis and cell cycle phenotype observed is specific to SIL downmodulation.

Example 5

Identification of Additional Sirna Sequences for Inhibition of Various Cancers

As is shown in Example 3 and FIG. 6a, exposure of the LS 174T clones to Tetracycline caused a reduction in cell number that correlated with the magnitude of SIL downregulation. To test if additional siRNA sequences can cause a similar effect on cancerous cells, and in addition, to demonstrate the feasibility of soluble siRNA agents in inhibiting the growth of cancerous cells, the present inventors have designed additional siRNA sequences [1207 (SEQ ID NO:14), 2163 (SEQ ID NO:15) and a scrambled sequence (SEQ ID NO:23)].

Experimental Results

Transient transfection of the two soluble siRNA oligonucleotides [1207 (SEQ ID NO:14) and 2163 (SEQ ID NO:15)] into 293T cells resulted in significant decreases in SIL RNA levels as compared to transfection with the scrambled oligonucleotide (5'-acugcguaccaucgugcc; SEQ ID NO:23).

Moreover, as is further shown in FIG. 6b, transient transfection of the soluble siRNA oligonucleotides [1207 (SEQ ID NO:14) and 2163 (SEQ ID NO:15)] into eight other cancer cell lines; MCF-7 (breast adenocarcinoma), PANC 1 (pancreas carcinoma), U-87 (glioblastoma), Caki-2 (kidney carcinoma), H1299 (Non Small Cell Lung Carcinoma), HeLa (cervix adenocarcinoma), PC3 (prostate adenocarcinoma), resulted in significant inhibition of cancerous cell growth.

Thus, these results demonstrate that inhibition of SIL using soluble siRNA oligonucleotides is efficient in inhibiting the growth of cancerous cells.

Example 6

SIL is a Target of E2F

To test the hypothesis that SIL might be an E2F1 target gene, the gene expression data derived from several studies designed to find E2F1 direct target genes (15-17) was searched. Either ectopic overexpression of E2F1 or silencing of the Rb gene (which leads to activation of the endogenous E2F (18), resulted in a rise of SIL mRNA levels, in a pattern similar to other mitotic checkpoint genes (Table 2, hereinbelow). To further verify this finding the present inventors used the previously described WI-38 embryonic lung fibroblasts transfected with an inducible E2F1(ER-E2F1) that is activated upon addition of 4-hydroxytamoxifen (OHT) to the growth medium (19). The activation of E2F1 was associated with a rise in the levels of SIL mRNA (FIG. 19a). To assure the rise in SIL levels is not falsely caused by an ectopic over-expression of E2F1, the present inventors examined its levels after activation of the endogenous E2Fs by ectopic expression of E1A, which is a viral oncoprotein that binds Rb and consequently activates the endogenous E2F (20). SIL mRNA levels were elevated in cells transfected with E1A, supporting its regulation by endogenous E2Fs (FIG. 19b). To examine whether E2F1 downregulation can cause a decrease in SIL expression levels, a T-cell leukemic cell line was infected with either shRNA for E2F1 or with nonspecific shRNA. Knockdown of E2F1 resulted in decreased SIL expression (FIG. 19c). Thus the expression of SIL depends on the levels of active E2F1. These results demonstrate that SIL is regulated by E2F.

TABLE 2

Selected genes induced upon Rb knockdown

| Name | FC | SD | E2F site |
|---|---|---|---|
| SIL | 2.93 | 0.36 | + |
| ZWINT | 3.64 | 0.24 | + |
| TTK | 3.6 | 0.44 | + |
| MAD2 | 4.16 | 0.95 | + |
| CYCLIN B | 3.66 | 0.22 | − |
| CYCLIN E | 5.27 | 0.81 | + |

Endogenous E2Fs Binds SIL Promoter In-Vivo—

The SIL promoter was previously described (21) to have two E2F1 binding sites in a region conserved between human and mouse. To determine if these binding sites are functional, a chromatin immunoprecipitation assay (ChIp) was performed. Jurkat cells (human T lymphocyte cell line) crosslinked and immunoprecipitated with antibodies against E2F1, E2F2, E2F3, E2F4, and HA were used as a template for PCR amplification of SIL. Negative (no DNA) and positive (input DNA representing 0.2% of total input chromatin) control amplifications are shown (FIG. 19d). SIL primers were constructed from the promoter containing an E2F1 binding site, and also from exon 12, not containing an E2F1 binding site (negative control). The results show that E2F, especially E2F1 and E2F4, bind the SIL promoter in-vivo. Thus SIL is an E2F regulated gene.

Analysis and Discussion:

It is presently disclosed for the first time that RNAi-mediated knockdown of SIL in cell lines derived from different cancer types (see Examples 1 and 2 above) generates the same striking phenotype: block of mitotic entrance coupled with apoptosis and growth cessation. Thus, the requirement of SIL for survival and cell division is relevant to cancer in general. This conclusion is supported by the ubiquitous expression of SIL in cancer cells and its regulation during mitosis. Moreover, it has been recently demonstrated (not shown) that SIL is a target of E2F, a transcription factor uniformly activated in cancer.

A potential concern is that SIL may be required for survival of normal cells. SIL knockout mice die during embryogenesis. However SIL knockout embryonic stem cells proliferate normally and form teratomas in mice (Izraeli, S. et al., 1999. Nature 399: 691-4). The present inventors have also generated an embryonic fibroblast SIL knockout cell line (unpublished). These observations suggest that SIL may not be universally required for cell proliferation and survival. Moreover, SIL is not expressed in non-dividing cells. Therefore, the potential toxicity of SIL knockdown is probably similar to other chemotherapeutic agents, namely transient bone-marrow suppression. Given the high therapeutic ratio of other anti-mitotic drugs, the expression of SIL in normal proliferating cells does not contraindicate its use as a target for anti-cancer and anti-mitotic therapy. Furthermore, since it is presently convincingly shown that inhibition of SIL expression can be used to inhibit in-vivo growth of human cancer cells in a mammal, it can be concluded that small molecules capable of inhibiting SIL and SIL-mediated biochemical pathways can be used for therapy, similarly to the presently described RNAi-based method of inhibiting SIL.

The present inventors have demonstrated the requirement of SIL for cancer cells survival and mitotic entry. Previous studies by the present inventors showed increased expression of SIL in parallel with other mitotic check point genes in tumors with increased mitotic activity and mitotic index. The finding that the mitotic check point gene MAD2, which was highly correlated with SIL expression in lung cancer, is regulated by E2F, led to investigate whether SIL overexpression in tumors could be a reflection of the activity of E2F. Datamining of published microarray data (15-17) showed that SIL was co-regulated by E2F together with other G2/M phase genes. In addition, it is shown here that SIL mRNA is increased upon activation of the endogenous E2F1 and is reduced by silencing E2F1. Lastly, the results presented here demonstrate that E2F1 binds to the SIL promoter in vivo. Thus SIL is regulated by E2F1.

The Rb/E2F pathway is known to be universally disrupted in cancer leading to loss of growth control (24). The role of E2F in prompting G1/S transition during the cell cycle has been well documented. Recently, a role for E2F in regulation of mitosis has been suggested (Giangrande, P. H 2004). Reis and Edgar proposed that E2F target genes, by acting on both the G1/S and G2/M transitions, enable cells to maintain normal proliferation rates by altering the length of G2 in response to alterations in the length of G1 (25). Thus, E2F target genes coordinate the transitions necessary for cell cycle progression both at the G1/S and the G2/M boundaries. When one E2F mitotic target gene i.e., MAD2 is aberrantly expressed due to abnormal activation of E2F, cells suffer from mitotic defects leading to aneuploidy (14).

To elucidate the role of SIL in cancer cells the present inventors have generated an inducible knockdown of the endogenous human SIL. The results show that SIL is necessary for survival of L174T colon cancer cells in-vitro and in-vivo, in a manner that correlates with its levels of expression. Interestingly, examination of explant tumors in mice that escape the growth suppression of Tetracycline reveals normal expression of SIL. These findings suggest that SIL is essential for tumor growth and that the tumor escape is caused by "takeover" of cells in which the shRNA was probably silenced or lost. The apoptosis induced in the absence of SIL does not depend on an intact P53 pathway as it is observed as well it in P53 deficient cell lines transfected with the SIL specific siRNA oligos. The specificity of the knockdown phenotype was confirmed by successful rescue with a construct encoding the mouse Sil.

In addition to induction of apoptosis, SIL knockdown resulted in a substantial reduction of mitotic entry. Using morphological, FISH and biochemical analyses the present inventors demonstrated that, in the absence of SIL, cells delay their entry to mitosis and undergo apoptosis. This phenotype was most pronounced upon treatment with chemical agents that cause metaphase arrest (colchicine and taxol). SIL is also necessary for the timely activation of CDK1 (CDC2), the major kinase regulating mitotic entry (26, 27). SIL may either directly regulate the activation of CDK1 or it may work further upstream. The rescuability of the knockdown system by constructs encoding the mouse Sil provides a useful system to further characterize the structural elements in SIL mediating these mitotic and apoptotic phenotypes.

The present inventors have recently demonstrated that SIL is phosphorylated during mitosis on several conserved serine/threonine residues (7). This mitotic phosphorylation is necessary for interactions with the mitotic regulator PIN1. Unlike the knockdown phenotype, HeLa cells over expressing a SIL mutated in these phosphorylation sites ("SIL IIP") enter mitosis properly and do not exhibit increased levels of apoptosis. However, upon prolonged exposure to taxol they escape the mitotic arrest and return to a "G2 like" state ("mitotic slippage"). Thus it seems that the mitotic phosphorylation of SIL is not important for its pro-survival function at mitotic entry. This conclusion is strengthened by preliminary experiments that demonstrate that SIL IIP rescues the apoptosis phenotype of LS174T cells with knockdown of the endogenous SIL (Castiel & Izraeli data not shown).

The present inventors have reported here the novel discovery that SIL functions in a "checkpoint" coupling the transition into mitosis with cell survival in variety of cancer cells. SIL is not necessary for survival for all cells. Mouse embryonic stem cells lacking any functional Sil protein proliferate normally and create teratomas in nude mice (5). Although mitosis is a general physiological process, cancer cells are highly sensitive to anti mitotic drugs. Indeed the therapeutic rations of drugs such Taxol and Vincristine is surprisingly high. Consequently, there is a marked effort to develop new drugs targeting molecules that regulate mitosis and mitotic entry (28, 29). As the SIL protein regulates mitotic entry and cell survival, it may prove a target for novel anti cancer therapeutics, especially for tumors in which E2F1 is activated.

Conclusion:

The above-described results convincingly and surprisingly demonstrate for the first time that downmodulation of SIL can be used to inhibit in a mammal the growth of tumors, such as gastrointestinal tumors, specifically human colon cancer, lung cancer, cervical cancer, prostate cancer and breast cancer, pancreatic cancer and glioblastoma. As such, the presently disclosed results teach for the first time that inhibition of SIL expression can be used to treat in a human a disease associated with abnormal cell proliferation, such as cancer, autoimmune proliferative disorders [e.g., rheumatoid arthritis (proliferative synovitis) and viral (e.g., EBV)-induced lymphoid proliferation], psoriasis, proliferative retinitis and ulcerative colitis. It will be appreciated that the presently disclosed method, by virtue of involving specific transfection of tumor cells with an inducible SIL siRNA expression vector, advantageously enables effective, specific and safe delivery of SIL siRNA to tumor cells, while avoiding inefficient drug delivery and/or bystander cell toxicity associated with systemic delivery of prior art cancer drugs such as mitosis-blocking drugs.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications and sequences identified by their GenBank accession numbers mentioned in this specification are herein incorporated in their entirety by reference into the specification, to the same extent as if each individual publication or sequence identified by its GenBank accession number was specifically and individually indicated to be incorporated herein by reference. In addition, citation or identification of any reference in this application shall not be construed as an admission that such reference is available as prior art to the present invention.

REFERENCES

Additional References are Cited in Text

1. Aplan P D, L. D., Ginsberg A M, Cossman J, Bertness V L, Kirsch I R. 1990. Disruption of the human SCL locus by "illegitimate" V-(D)-J recombinase activity. SCIENCE 250:1426-1429.
2. Aplan P D, L. D., Kirsch I R. 1991. Structural characterization of SIL, a gene frequently disrupted in T-cell acute lymphoblastic leukemia. Mol Cell Biol 11:5462-5469.
3. Collazo-Garcia N, S. P., Aplan P D. 1995. Cloning and characterization of a murine SIL gene. Genomics 30:506-513.
4. Golling G, A. A., Sun Z, Antonelli M, Maldonado E, Chen W, Burgess S, Haldi M, Artzt K, Farrington S, Lin S Y, Nissen R M, Hopkins N. 2002. Insertional mutagenesis in zebrafish rapidly identifies genes essential for early vertebrate development. Nat Genet 31:135-140.
5. Izraeli, S., Lowe, L. A., Bertness, V. L., Good, D. J., Dorward, D. W., Kirsch, I. R., and Kuehn, M. R. 1999. The SIL gene is required for mouse embryonic axial development and left-right specification. Nature 399:691-694.
6. Izraeli, S., Colaizzo-Anas, T., Bertness, V. L., Mani, K., Aplan, P. D., and Kirsch, I. R. 1997. Expression of the SIL gene is correlated with growth induction and cellular proliferation. Cell Growth Differ 8:1171-1179.
7. Campaner S, K. P., Izraeli S, Kirsch I R. 2005. Sil phosphorylation in a Pin1 binding domain affects the duration of the spindle checkpoint. Mol Cell Biol 25:6660-6672.
8. Erez A, P. M., Hewitt S M, Cojacaru G, Goldberg I, Shahar I, Yaron P, Muler I, Campaner S, Amariglio N, Rechavi G, Kirsch I R, Krupsky M, Kaminski N, Izraeli S. 2004. Sil overexpression in lung cancer characterizes tumors with increased mitotic activity. Oncogene. 23:5371-5377.
9. Ramaswamy S, R. K., Lander E S, Golub T R. 2003. A molecular signature of metastasis in primary solid tumors. Nat Genet 33:49-54.
10. Ryan, L. B. a. K. 2004. Life and death decisions by E2F-1. Cell Death and Differentiation 11:137-142.
11. Ishida S, H. E., Zuzan H, Spang R, West M, Nevins J R. 2001. Role for E2F in control of both DNA replication and mitotic functions as revealed from DNA microarray analysis. Mol Cell Biol 21:4684-4699.
12. Polager S, K. Y., Berkovich E, Ginsberg D. 2002. E2F up-regulate expression of genes involved in DNA replication, DNA repair and mitosis. Oncogene 21:437-446.
13. Giangrande P H, Z. W., Schlisio S, Sun X, Mori S, Gaubatz S, Nevins J R. 2004. A role for E2F6 in distinguishing G1/S- and G2/M specific transcription. Genes Dev 18:2941-2951.
14. Hernando E, N. Z., Juan G, Diaz-Rodriguez E, Alaminos M, Hemann M, Michel L, Mittal V, Gerald W, Benezra R, Lowe S W, Cordon-Cardo C. 2004. Rb inactivation promotes genomic instability by uncoupling cell cycle progression from mitotic control. Nature 430:797-802.
15. Muller, H., Bracken, A. P., Vernell, R., Moroni, M. C., Christians, F., Grassilli, E., Prosperini, E., Vigo, E., Oliner, J. D., and Helin, K. 2001. E2Fs regulate the expression of genes involved in differentiation, development, proliferation, and apoptosis. Genes Dev 15:267-285.
16. Semizarov, D., Kroeger, P., and Fesik, S. 2004. siRNA-mediated gene silencing: a global genome view. Nucleic Acids Res 32:3836-3845.
17. Vernell, R., Helin, K., and Muller, H. 2003. Identification of target genes of the p16INK4A-pRB-E2F pathway. J Biol Chem 278:46124-46137.
18. Sellers W R, K. W. J. 1997. Role of the retinoblastoma protein in the pathogenesis of human cancer. J Clin Oncol 15:3301-3312.
19. Vigo E, M. H., Prosperini E, Hateboer G, Cartwright P, Moroni M C, Helin K. 1999. CDC25A phosphatase is a target of E2F and is required for efficient E2F-induced S phase. Mol Cell Biol 19:6379-6395.
20. Peeper D S, Z. A. 1993. Adenovirus-E1A proteins transform cells by sequestering regulatory proteins. Mol Biol Rep. 17:197-207.
21. Colaizzo-Anas, T., and Aplan, P. D. 2003. Cloning and characterization of the SIL promoter. Biochim Biophys Acta 1625:207-213.
22. van de Wetering M, O. I., Muncan V, Pon Fong M T, Brantjes H, van Leenen D, Holstege F C, Brummelkamp T R, Agami R, Clevers H. 2003. Specific inhibition of gene expression using a stably integrated, inducible small-interfering-RNA vector. EMBO Rep. 4:609-615.
23. Bridge A J, P. S., Ducraux A, Nicoulaz A L, Iggo R. 2003. Induction of an interferon response by RNAi vectors in mammalian cells. Nat Genet 34:263-264.
24. Fang Z H, H. Z. 2006. The transcription factor E2F: a crucial switch in the control of homeostasis and tumorigenesis. Histol Histopathol 21:403-413.
25. Reis T, E. B. 2004. Negative regulation of dE2F1 by cyclin-dependent kinases controls cell cycle timing. Cell 117:253-264.
26. S, F. 2006. Protein kinases controlling the onset of mitosis. Cell Mol Life Sci. 63:781-795.
27. Riabowol K, D. G., Brizuela L, Vandre D, Beach D. 1989. The cdc2 kinase is a nuclear protein that is essential for mitosis in mammalian cells. Cell 57:393-401.
28. Weaver B A, C. D. 2005. Decoding the links between mitosis, cancer, and chemotherapy: The mitotic checkpoint, adaptation, and cell death. Cancer Cell 8:7-12.
29. Rajagopalan H, L. C. 2004. Aneuploidy and cancer. Nature 432:338-341.
30. Chaussepied M, G. D. 2004. Transcriptional regulation of AKT activation by E2F. Mol Cell 16:831-837.
31. Brummelkamp, T. R., Bernards, R., and Agami, R. 2002. A system for stable expression of short interfering RNAs in mammalian cells. Science 296:550-553.
32. Raanani P, B.-B. I., Gan S, Trakhtenbrot L, Mark Z, Ashur-Fabian O, Itskovich S, Brok-Simoni F, Rechavi G, Amariglio N, Nagler A. 2004. Assessment of the response to imatinib in chronic myeloid leukemia patients—comparison between the FISH, multiplex and RT-PCR methods. Eur J Haematol 73:243-250.
33. Andreassen, P. R., and Margolis, R. L. 1994. Microtubule dependency of p34cdc2 inactivation and mitotic exit in mammalian cells. J Cell Biol 127:789-802.
34. Esa, A., Trakhtenbrot, L., Hausmann, M., Rauch, J., Brok-Simoni, F., Rechavi, G., Ben-Bassat, I., and Cremer, C. 1998. Fast-FISH detection and semi-automated image analysis of numerical chromosome aberrations in hematological malignancies. Anal Cell Pathol 16:211-222.

---

What is claimed is:

1. A method of treating a cancer comprising administering to a subject in need thereof a therapeutically effective amount of at least one modulator which decreases or eliminates a level and/or activity of a polypeptide comprising the amino acid sequence set forth in SEQ ID NO: 5, thereby treating the cancer in the subject, wherein said modulator is selected from the group consisting of an siRNA molecule which induces degradation or inhibits translation of an mRNA encoding said polypeptide and an antisense polynucleotide which hybridizes with an mRNA encoding said polypeptide.

2. The method of claim 1, wherein said siRNA molecule has a sense strand corresponding to a nucleotide sequence which comprises SEQ ID NO: 1, 2, 14 and/or 15.

3. The method of claim 1, wherein said administering said at least one modulator to the subject is effected by administering to the subject at least one nucleic acid construct which comprises at least one polynucleotide encoding said at least one modulator.

4. The method of claim 1, wherein the cancer is selected from the group consisting of a colorectal cancer, a uterine cervical cancer, a pancreatic cancer, a mammary cancer, a prostate cancer, a pulmonary cancer and a neurological cancer.

5. A method of regulating proliferation of a cell population which proliferates abnormally, the method comprising contacting the cell population with at least one modulator which decreases or eliminates in the cell population a level and/or activity of a polypeptide comprising the amino acid sequence set forth in SEQ ID NO: 5, thereby regulating proliferation of the cell population, wherein said modulator is selected from the group consisting of an siRNA molecule which induces degradation or inhibits a translation of an mRNA encoding said polypeptide and an antisense polynucleotide which hybridizes with an mRNA encoding said polypeptide.

6. The method of claim 5, wherein said siRNA molecule has a sense strand corresponding to a nucleotide sequence which comprises SEQ ID NO: 1, 2, 14 or 15.

7. The method of claim 5, wherein said administering said at least one modulator to the cell population is effected by administering to the cell population at least one nucleic acid construct which comprises at least one polynucleotide encoding said at least one modulator.

8. The method of claim 5, wherein the cell population is of a lineage selected from the group consisting of a gastrointestinal lineage, a uterine lineage, a glandular lineage, a pulmonary lineage and a neurological lineage.

9. The method of claim 5, wherein the cell population is of a lineage selected from the group consisting of a colorectal lineage, a uterine cervical lineage, a pancreatic lineage, a mammary lineage, a pulmonary epithelial lineage, a keratinocyte cell lineage and a glial lineage.

10. The method of claim 1, wherein the cancer is of a lineage selected from the group consisting of a gastrointestinal lineage, a uterine lineage, a glandular lineage, a pulmonary lineage and a neurological lineage.

* * * * *